US012029702B2

(12) United States Patent
Goldstein

(10) Patent No.: US 12,029,702 B2
(45) Date of Patent: Jul. 9, 2024

(54) THERAPEUTIC WAND SYSTEM, KIT, AND METHOD

(71) Applicant: Touch + Glow, Inc., New York, NY (US)

(72) Inventor: Shelley Phyllis Goldstein, New York, NY (US)

(*) Notice: Subject to any disclaimer, the term of this patent is extended or adjusted under 35 U.S.C. 154(b) by 0 days.

(21) Appl. No.: 15/641,842

(22) Filed: Jul. 5, 2017

(65) Prior Publication Data

US 2018/0008512 A1 Jan. 11, 2018

Related U.S. Application Data

(60) Provisional application No. 62/360,538, filed on Jul. 11, 2016.

(51) Int. Cl.
*A61H 39/04* (2006.01)
*A61H 23/02* (2006.01)
*A61N 2/00* (2006.01)

(52) U.S. Cl.
CPC ......... *A61H 39/04* (2013.01); *A61H 23/0263* (2013.01); *A61N 2/002* (2013.01);
(Continued)

(58) Field of Classification Search
CPC ...... A61H 39/00; A61H 39/04; A61H 39/007; A61H 2201/10; A61H 2201/153;
(Continued)

(56) References Cited

U.S. PATENT DOCUMENTS

| 4,574,787 A | 3/1986 | Jacobs | |
| 5,030,196 A * | 7/1991 | Inoue | A61N 2/02 361/143 |

(Continued)

FOREIGN PATENT DOCUMENTS

| CN | 104873367 | 9/2015 |
| WO | 01/80942 | 11/2001 |

(Continued)

OTHER PUBLICATIONS

Zhang, Y. et al. "Training Self-Administered Exercise among Postmenopausal women with Osteoarthritic Knee Pain: A Feasibility Study and Lessons Learned." Evidence-Based Complementary and Alternative Medicine, 2012. vol. 12, pp. 1-9.*
Feb. 2018 Eligibility Quick Reference Sheet https://www.uspto.gov/sites/default/files/documents/ieg-qrs.pdf.*
Tru Energy, All-Natural FaceLift Regime Instruction Guide, Jacksonville, Florida.

(Continued)

*Primary Examiner* — Colin W Stuart
*Assistant Examiner* — Douglas Y Sul
(74) *Attorney, Agent, or Firm* — Womble Bond Dickinson (US) LLP

(57) ABSTRACT

Embodiments of the present disclosure include a system for applying therapeutic pressure to a skin surface including a tip arranged at a first end of a therapeutic wand. The system also includes a head arranged opposite the tip at a second end of the therapeutic wand. The system includes a body arranged between the tip and the head, the body housing a control system for controlling operation of the therapeutic wand. The control system includes a printed circuit board, a timer electrically connected to the printed circuit board, the timer being programmable to determine an elapsed time of use of the therapeutic wand, and an indicator. The system also includes a grip arranged between the body and the head, the grip having an outer surface that is softer than the body to provide an ergonomic and comfortable location to hold the therapeutic wand.

11 Claims, 31 Drawing Sheets

(52) U.S. Cl.
CPC .. *A61H 2201/0153* (2013.01); *A61H 2201/10* (2013.01); *A61H 2201/169* (2013.01)

(58) Field of Classification Search
CPC .... A61H 39/02; A61H 23/02; A61H 15/0078; A61H 15/0085
See application file for complete search history.

(56) References Cited

U.S. PATENT DOCUMENTS

| | | | |
|---|---|---|---|
| 5,113,847 A | 5/1992 | Holzworth | |
| 5,224,469 A * | 7/1993 | Mocny | A61H 39/04 600/587 |
| 5,542,907 A * | 8/1996 | Chou | A61H 23/0263 601/46 |
| 5,577,995 A | 11/1996 | Walker et al. | |
| 5,720,046 A | 2/1998 | Lopez et al. | |
| 5,782,858 A * | 7/1998 | Cheng | A61N 2/06 606/189 |
| 5,792,176 A | 8/1998 | Chang | |
| 5,950,239 A | 9/1999 | Lopez | |
| 6,102,875 A | 8/2000 | Jones | |
| 6,182,313 B1 | 2/2001 | Eschenbach | |
| 6,193,740 B1 | 2/2001 | Rodriguez | |
| 6,237,603 B1 | 5/2001 | Mendell | |
| 6,258,020 B1 | 7/2001 | Lopez | |
| 6,261,306 B1 | 7/2001 | Kramer | |
| 6,297,719 B1 | 10/2001 | Miller | |
| 6,299,586 B1 | 10/2001 | Cao | |
| 6,419,650 B1 | 7/2002 | Ryan et al. | |
| 6,450,945 B1 | 9/2002 | Mendell | |
| 6,458,146 B1 | 10/2002 | Kramer | |
| 6,676,686 B2 | 1/2004 | Naganuma | |
| 6,679,825 B2 * | 1/2004 | Alicea | A61N 2/008 600/9 |
| 6,820,574 B2 | 11/2004 | Sharpe | |
| 6,860,896 B2 | 3/2005 | Leber et al. | |
| 6,866,776 B2 | 3/2005 | Leason et al. | |
| 6,988,997 B2 | 1/2006 | Stultz | |
| 7,335,170 B2 * | 2/2008 | Milne | A61H 7/001 601/15 |
| 7,441,516 B2 | 10/2008 | Sharpe | |
| 7,473,217 B2 | 1/2009 | Oh | |
| 7,632,217 B2 | 12/2009 | Rooney | |
| D657,065 S | 4/2012 | Matsushita | |
| D666,304 S | 8/2012 | Matsushita | |
| 8,523,754 B2 | 9/2013 | Bechler et al. | |
| 8,602,962 B2 | 12/2013 | Gavish et al. | |
| 8,626,265 B2 | 1/2014 | Hempel et al. | |
| 8,718,758 B2 | 5/2014 | Wagner et al. | |
| 8,764,620 B2 | 7/2014 | Bechler et al. | |
| 8,886,304 B2 | 11/2014 | Wagner et al. | |
| 8,892,200 B2 | 11/2014 | Wagner et al. | |
| 8,897,871 B2 | 11/2014 | Wagner et al. | |
| 8,898,840 B1 | 12/2014 | Majette | |
| 8,929,979 B2 | 1/2015 | Wagner et al. | |
| 8,977,354 B2 | 3/2015 | Wagner et al. | |
| 9,050,463 B2 | 6/2015 | Wagner | |
| 9,113,985 B2 | 8/2015 | Bechler et al. | |
| 9,333,145 B2 | 5/2016 | Cho et al. | |
| 2001/0047186 A1 | 11/2001 | Cao | |
| 2002/0002387 A1 | 1/2002 | Naganuma | |
| 2002/0151930 A1 | 10/2002 | Mills | |
| 2003/0074020 A1 | 4/2003 | Kramer | |
| 2004/0044384 A1 | 3/2004 | Leber et al. | |
| 2004/0230256 A1 * | 11/2004 | Lin-Hendel | A61H 39/002 607/72 |
| 2005/0013851 A1 | 1/2005 | Sharpe | |
| 2005/0070977 A1 | 3/2005 | Molina | |
| 2006/0149119 A1 | 7/2006 | Wang | |
| 2006/0178715 A1 * | 8/2006 | Ahn | A61H 39/002 607/96 |
| 2006/0211959 A1 | 9/2006 | Oh | |
| 2006/0235341 A1 * | 10/2006 | Feng | A61H 23/0263 601/15 |
| 2006/0270956 A1 * | 11/2006 | Wong | A61H 39/04 601/108 |
| 2007/0060447 A1 | 3/2007 | Rooney | |
| 2007/0084470 A1 | 4/2007 | Sarazen | |
| 2007/0104694 A1 | 5/2007 | Quijano | |
| 2008/0195181 A1 | 8/2008 | Cole | |
| 2008/0306508 A1 | 12/2008 | Spector | |
| 2008/0319358 A1 * | 12/2008 | Lai | A61H 39/04 601/134 |
| 2009/0076422 A1 * | 3/2009 | Wong | A61H 39/04 601/134 |
| 2009/0306561 A1 | 12/2009 | Naganuma | |
| 2011/0178360 A1 | 7/2011 | Gavish et al. | |
| 2011/0218421 A1 | 9/2011 | Hempel et al. | |
| 2012/0108884 A1 | 5/2012 | Bechler et al. | |
| 2012/0143081 A1 * | 6/2012 | Lyu | A61B 5/4824 600/557 |
| 2012/0158042 A1 * | 6/2012 | Cho | A61H 39/04 606/204 |
| 2013/0053733 A1 * | 2/2013 | Korb | A61H 9/0057 601/2 |
| 2013/0245509 A1 | 9/2013 | Tanigawa et al. | |
| 2013/0317278 A1 | 11/2013 | Bechler et al. | |
| 2014/0012152 A1 | 1/2014 | Gentry et al. | |
| 2014/0213945 A1 * | 7/2014 | Kojima | A61H 39/04 601/137 |
| 2014/0249354 A1 * | 9/2014 | Anderson | A61N 2/004 600/14 |
| 2014/0277582 A1 * | 9/2014 | Leuthardt | A61F 2/54 623/25 |
| 2014/0335476 A1 | 11/2014 | Bechler et al. | |
| 2015/0119771 A1 * | 4/2015 | Roberts | A61H 39/04 601/135 |
| 2015/0374578 A1 * | 12/2015 | Matsuura | A61H 23/0263 601/46 |
| 2016/0338903 A1 * | 11/2016 | Yang | A61H 23/0263 |

FOREIGN PATENT DOCUMENTS

| | | |
|---|---|---|
| WO | 02/22224 | 3/2002 |
| WO | 03/061545 | 7/2003 |
| WO | 2004/096343 | 11/2004 |
| WO | 2006/116728 | 11/2006 |
| WO | 2007/049896 | 5/2007 |
| WO | 2007/071295 | 6/2007 |
| WO | 2008/052346 | 5/2008 |
| WO | 2015038005 | 3/2015 |
| WO | 2015/084263 | 6/2015 |
| WO | 2015/129435 | 3/2017 |

OTHER PUBLICATIONS

Screenshot from Tru Energy website, How Toxins Can Affect Your Body, https://www.truenergyskincare.com/blogs/news, Oct. 14, 2015.
Screenshot from YouTube, This Is a Magic Wand, Tru Energy, https://www.youtube.com/watch?v=IYb1oCX2UHA, Oct. 14, 2015.
Screenshot from Vimeo, Tru Energy, https://vimeo.com/133856219, Approx. Jun. 2015.
International Search Report and Written Opinion for PCT/US2017/041217, Oct. 24, 2017.
Goldstein, Shellie, Your Best Face Now, Copyright 2012 by Hamptons Acupuncture, Penguin Group, New York, NY.

* cited by examiner

THERAPEUTIC WAND SYSTEM, KIT, AND METHOD

RELATED APPLICATION

This application claims priority to and the benefit of U.S. Provisional Patent Application No. 62/360,538 filed on Jul. 11, 2016 titled "Therapeutic Wand System, Kit, and Method" and which is incorporated herein by reference in its entirety.

BACKGROUND

1. Field of the Invention

The present disclosure relates to beauty, health, and wellness products. More particularly, the present disclosure relates to a therapeutic wand for activation of acupressure points.

2. Description of Related Art

Acupuncture is a form of alternative or holistic medicine that involves stimulating locations of a body utilizing a needle or external pressure. In traditional Chinese medicine, life force energy, known as Qi or Chi, flows through the body through channels referred to as meridians (e.g., locations). The locations of the body (e.g., acupuncture and/or acupressure points) are often, but not always, located along these meridians (e.g., locations), and it is believed that stimulation of these locations promotes healing, beauty, and wellness.

Typically, acupuncture utilizes the insertion of thin needles at or near the meridians, which persons having a phobia of needles may find unpleasant. As a result, other methods, such as acupressure, have been developed to provide similar benefits without puncturing the skin. Acupressure points (often in the same location as acupuncture points) are physically manipulated, such as with a finger or device, to stimulate the points and receive the benefits described above. Typically, a licensed practitioner performs the procedures because laypersons may be unfamiliar with the acupressure points or how to properly manipulate the points. For example, laypersons may apply too much pressure or not apply pressure for long enough, thereby reducing the effectiveness of the treatments. Moreover, it may be difficult for laypersons to identify licensed, highly qualified individuals to perform the treatments. Accordingly, it is now recognized that it would be desirable to have a guided, at-home system to provide acupressure treatment.

SUMMARY

Applicants recognized the problems noted above herein and conceived and developed embodiments of system, kit, and methods, according to the present disclosure, for at-home health, beauty, and wellness treatments.

In an embodiment a system for applying therapeutic pressure to a skin surface includes a tip arranged at a first end of a therapeutic wand, the tip having a substantially smooth surface. The system also includes a head arranged opposite the tip at a second end of the therapeutic wand. The system further includes a body arranged between the tip and the head, the body housing a control system for controlling operation of the therapeutic wand. The control system includes a printed circuit board, a timer electrically connected to the printed circuit board, the timer being programmable to determine an elapsed time of use of the therapeutic wand, and an indicator, the indicator positioned to receive a signal from the printed circuit board indicative of the passage of a predetermined period of time. The system also includes a grip arranged between the body and the head, the grip having an outer surface that is softer than the body to provide an ergonomic and comfortable location to hold the therapeutic wand.

In another embodiment an at-home health, beauty, and wellness therapeutic wand kit includes a container having a bed arranged therein to support one or more components of the kit. The bed includes an indentation in a surface of the container to receive and support the one or more components and provide protection during shipping and movement of the kit. The kit also includes a therapeutic wand for administering at-home health, beauty, and wellness treatments via activation of one or more acupressure points. The therapeutic wand is positioned within the bed of the container and separated from one or more components of the kit. Also, the kit includes an instruction booklet positioned within the container; the instruction booklet is separated from the therapeutic wand and arranged outside of the bed of the container.

In an embodiment an at-home health, beauty, and wellness therapeutic wand kit including a container for supporting one or more components of the kit. The container includes one or more compartments to receive and support the one or more components and provide protection during shipping and movement of the kit. The kit also includes a therapeutic wand for administering at-home health, beauty, and wellness treatments via activation of one or more acupressure points, the therapeutic wand being positioned within the one or more compartments. Also, the kit includes an instruction booklet positioned within the container and proximate the therapeutic wand.

In a further embodiment a method for operating an at-home therapeutic wand includes positioning a therapeutic wand proximate a first predetermined location, the first predetermined location corresponding to one or more acupressure points. The method also includes applying pressure to the first predetermined location via the therapeutic wand, the therapeutic wand comprising a tip that bears against a skin surface proximate the first predetermined location. The method further includes holding the therapeutic wand against the first predetermined location for a predetermined period of time, the predetermined period of time being signaled by an indicator positioned in the therapeutic wand. The method also includes moving the therapeutic wand to a second predetermined location, the second predetermined location corresponding to the one or more acupressure points and being spaced apart from the first predetermined location.

In a further embodiment, a method for operating an at-home therapeutic wand includes positioning a therapeutic wand proximate a first predetermined location, the first predetermined location corresponding to one or more acupressure points. The method also includes applying pressure to the first predetermined location via the therapeutic wand, the therapeutic wand comprising a tip that bears against a skin surface proximate the first predetermined location. The method further includes holding the therapeutic wand against the first predetermined location for a predetermined period of time. The method also includes moving the therapeutic wand to a second predetermined location, the second predetermined location corresponding to the one or more acupressure points and being spaced apart from the first predetermined location.

BRIEF DESCRIPTION OF DRAWINGS

The foregoing aspects, features, and advantages of the present disclosure will be further appreciated when considered with reference to the following description of embodiments and accompanying drawings. In describing the embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

DETAILED DESCRIPTION

Figure 1:
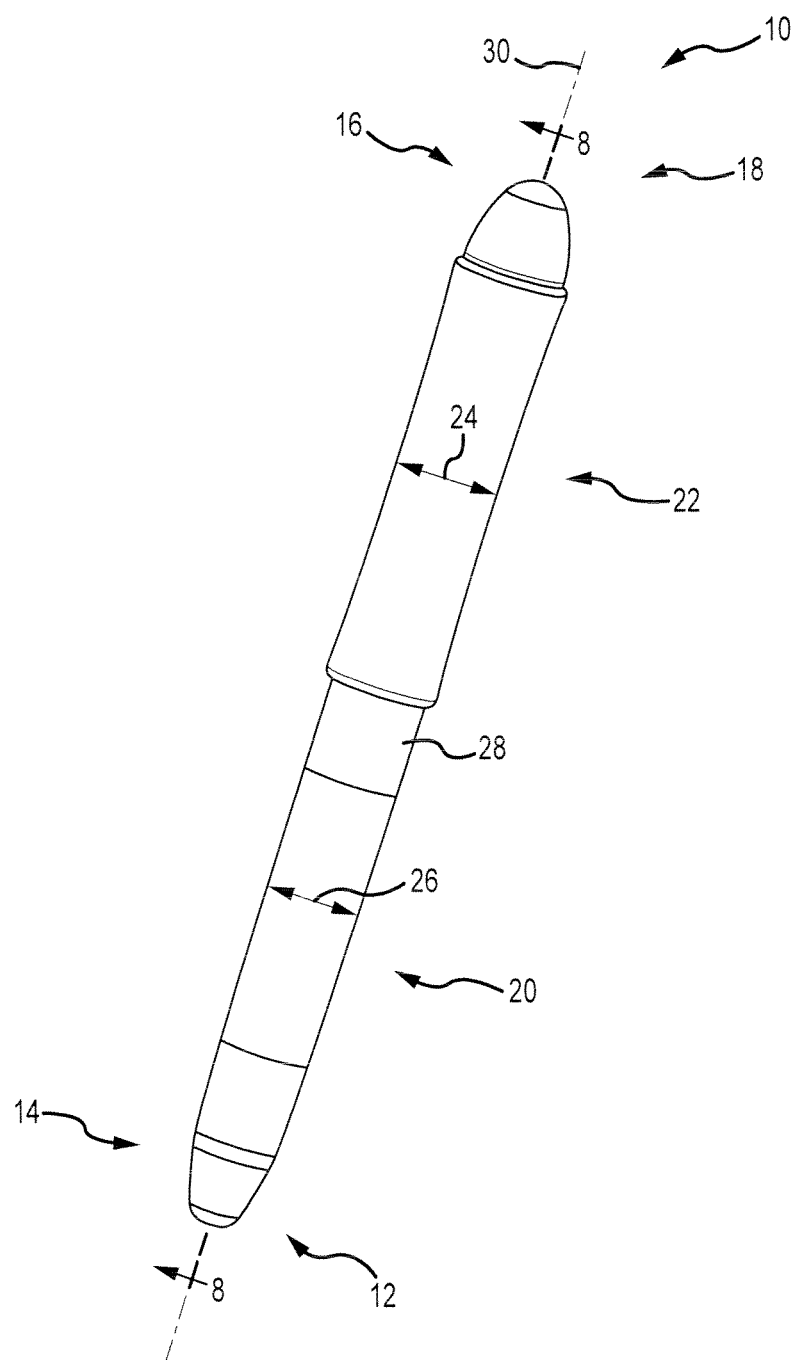
FIG. 1 is a front perspective view of an embodiment of a therapeutic wand, in accordance with embodiments of the present disclosure.

The foregoing aspects, features, and advantages of the present disclosure will be further appreciated when considered with reference to the following description of embodiments and accompanying drawings. In describing the embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments. Additionally, it should be understood that references to "one embodiment," "an embodiment," "certain embodiments," or "other embodiments" of the present disclosure are not intended to be interpreted as excluding the existence of additional embodiments that also incorporate the recited features. Furthermore, reference to terms such as "above," "below," "upper," "lower," "side," "front," "back," or other terms regarding orientation are made with reference to the illustrated embodiments and are not intended to be limiting or exclude other orientations.

Embodiments of the present disclosure include a therapeutic wand, a therapeutic wand kit, and methods of operation of the therapeutic wand. In certain embodiments, the therapeutic wand includes a tip, a body, and a head. The tip can be utilized to apply vibrational forces (e.g., generated by a motor within the therapeutic wand) to a skin surface, thereby improving circulation and lymph drainage to generate an improved physical appearance of the skin. In certain embodiments, the therapeutic wand includes one or more processors (such as a printed circuit board) and/or an indicator to transmit signals to a user. For example, the processor may determine the duration of time that the tip is pressed against the skin surface and send a signal to the indicator after a predetermined time to notify the user that the predetermined time has passed. In this manner, consistent and repeatable use of the therapeutic wand may be achieved. Furthermore, embodiments of the present disclosure include the therapeutic wand kit. The kit can include the therapeutic wand, a container, and an instruction booklet. The container may be arranged to receive the therapeutic wand and the instruction booklet. Moreover, in certain embodiments, the kit may further include replacement parts or a protective covering for the therapeutic wand. Additionally, embodiments of the present disclosure include methods of operation for the therapeutic wand. For example, the methods may include positioning the therapeutic wand at acupressure points, applying pressure to a skin surface, determining whether a predetermined period of time has passed, and moving the therapeutic wand after the predetermined period of time has passed. In this manner, the user can utilize the therapeutic wand to improve the physical appearance of the skin.

FIG. 1 is a front perspective view of an embodiment of a therapeutic wand 10 for use in at-home acupressure treatments. As will be described in detail below, the therapeutic wand 10 (e.g., wand, device, pen, etc.) can be used to apply pressure to one or more acupressure points on a human body, such as the face, neck, etc., to improve circulation and lymph drainage, among other benefits, to generate an improved physical appearance of the skin. As used herein, improved physical appearance refers to a reduction of fine lines or wrinkles, relaxed facial muscles, tighter-looking skin and deeper tissue, even skin tone, tighter pores, improved hydration, and/or a more youthful, energized, glowing appearance. In the illustrated embodiment, the therapeutic wand 10 has a generally cylindrical shape, much like the shape of a pencil or pen, to enable a user to easily and instinctively hold and handle the therapeutic wand 10. The therapeutic wand 10 includes a tip 12 at a first end 14 and a head 16 at a second end 18. As shown, the tip 12 and the head 16 are at opposite ends of the therapeutic wand 10. The illustrated therapeutic wand 10 further includes a body portion 20 connecting the first end 14 and the second end 18, as well as a grip 22 positioned proximate the head 16. That is, the grip 22 is positioned closer to the second end 18 than the first end 14. As illustrated, the grip 22 includes a larger grip outer diameter 24 than the body outer diameter 26, thereby enabling an easier and more comfortable surface for the user to hold and manipulate the therapeutic wand 10. In certain embodiments, the grip 22 may be formed from a material that is softer and more malleable than the body 20. For example, the body 20 can be metallic, such as a steel, steel alloy, or the like, while the grip 22 may be plastic, neoprene, cloth, synthetic, or a softer metal. As a result, the user can have an improved experience using the therapeutic wand 10 because the softer grip 22 is easier to hold and more ergonomic than the hard, metallic body 20. For example, the grip 22 also can be formed of a silicone material, as will be understood by those skilled in the art, and evenly weighted to enhance ease of holding by user when positioned in a hand of a user. In certain embodiments, the position of the grip 22 is particularly selected, relative to the length of the body 20, to balance the therapeutic wand 10. For example, the weight of the wand 10 may be anticipated by determining the weight of the components plus an energy source, such as a battery. Thereafter, a balance point for locating the grip 22 may be selected.

In the illustrated embodiment, the therapeutic wand 10 includes a switch 28 positioned along the body 20 and proximate the grip 22. As shown, the switch 28 is arranged close to a midpoint of the therapeutic wand 10. However, it should be appreciated the switch 28 may be arranged proximate the tip 12, proximate the head 16, or at any other location along the therapeutic wand 10. In the illustrated embodiment, the switch 28 is a twist switch that is activated by twisting the therapeutic wand 10 about a longitudinal axis 30 to turn on a motor or some other electrical device within the therapeutic wand 10. The twisting of the therapeutic wand 10 couples together circuitry within the therapeutic wand 10, as described in detail below, to activate an internal motor, electromagnet, processor, and the like. It should be appreciated that while the illustrated embodiment includes a twist switch, in other embodiments the switch 28 can be a tactile switch, an electric twitch, a pressure-activated switch, or any other suitable means for activating the internal components of the therapeutic wand 10. Therefore, as used herein, the switch 28 may be used to generally describe a mechanism for activating (e.g., turning on/off, changing operating parameters, etc.) one or more electronic components.

As shown, certain components of the therapeutic wand 10 are illustrated as being arranged in a generally side-by-side abutting relationship along the longitudinal axis 30 such that the components are co-axial with one another, as well as the longitudinal axis 30. For example, the tip 12 is arranged axially adjacent to the body 20, which is axially adjacent to the grip 22, which is further axially adjacent to the head 16. In certain embodiments, the components are connected together via threaded fittings. For example, the body 20 may include a threaded component (e.g., male or female threads), which is threadingly engaged with the grip 22. In certain embodiments, a battery arranged within the therapeutic wand 10 can be removed and replaced by disassembling the therapeutic wand 10 at the threaded connection, thereby permitting access to the interior of the therapeutic wand 10 and enabling the user to replace the battery. Moreover, in certain embodiments, the tip 12, the head 16, or another other component of the therapeutic wand 10 may include threads, clips, or the like to enable attachment and disassembly from the therapeutic wand 10. For example, as will be described below, the head 16 may include a precious stone, a semi-precious stone, a man-made stone, a mineral, or a metal that are believed to provide certain therapeutic benefits by alternative and holistic medicine practitioners. Moreover, in certain embodiments, the head 16 may include a therapeutic light emitting diode (LED). In certain embodiments, the therapeutic LED may be utilized along with the precious stone, semi-precious stone, man-made stone, mineral, or metal. That is, the head 16 may include some combination of therapeutic LED, precious stone, semi-precious stone, man-made stone, mineral, or metal. By having the head 16 arranged in a matter that enables disassembly, the user may change out the heads 16 to treat various ailments without obtaining multiple therapeutic wands 10. Similarly, the user may be able to replace the tip 12 if the tip 12 is threadingly engaged with the body 20. In this manner, various components of the therapeutic wand 10 can be replaced and/or switched out to increase the different uses of the therapeutic wand 10 and to enable troubleshooting and maintenance of the therapeutic wand 10.

Figure 2:
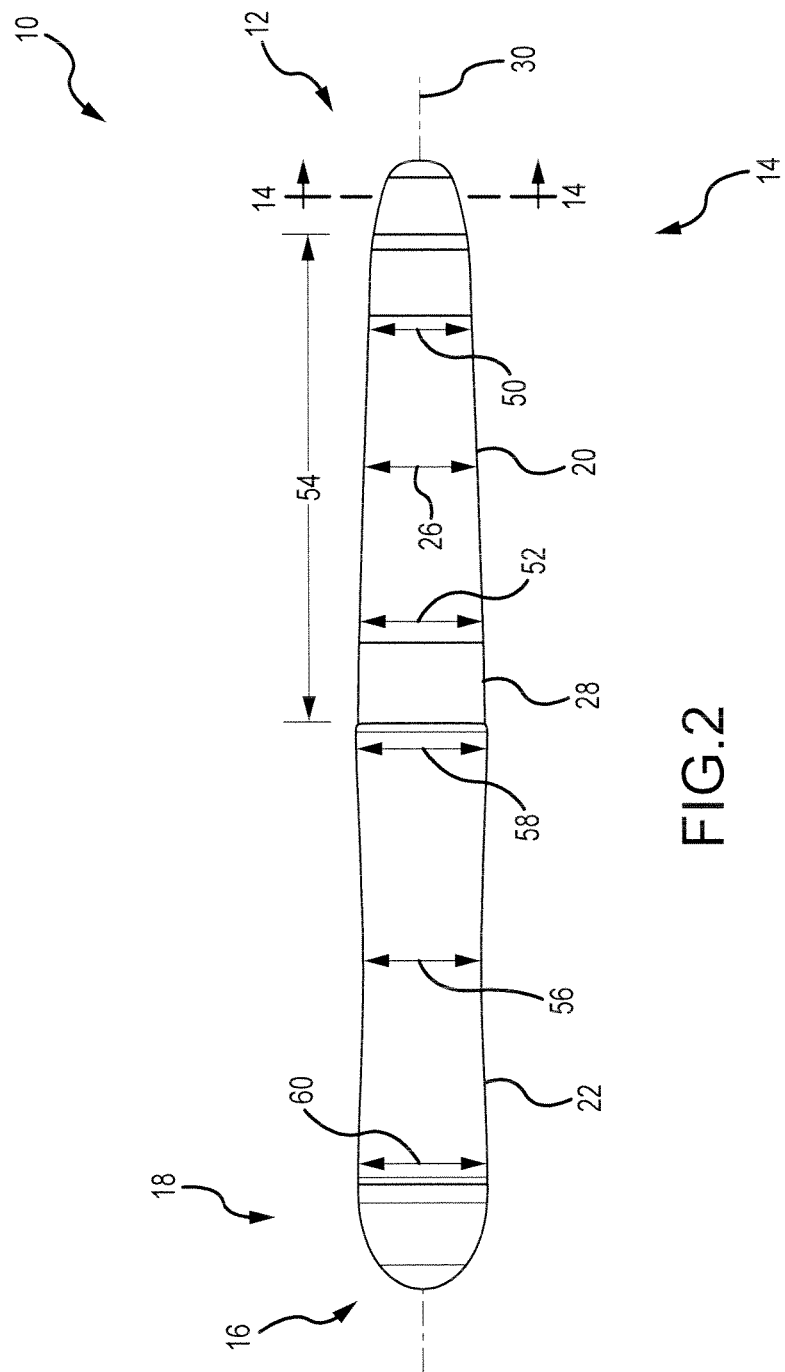
FIG. 2 is a side elevational view of the therapeutic wand of FIG. 1 having a twist switch, in accordance with embodiments of the present disclosure.

FIG. 2 is a side elevational view of the therapeutic wand 10. As described above, the tip 12 is arranged at the first end 14 opposite the head 16 at the second end 18. In the illustrated embodiment, the body outer diameter 26 changes along the longitudinal axis 30. That is, a first body outer diameter 50 proximate the tip 12 is smaller than a second body outer diameter 52 proximate the grip 22. As such, the body outer diameter 26 changes along a length 54 of the body 20. However, it should be appreciated that, in certain embodiments, the body outer diameter 26 can remain constant along the length 54 of the body 20.

As described above, the grip 22 is positioned proximate the body 20 and formed so as to provide a comfortable, ergonomic position for the user to hold the therapeutic wand 10. In certain embodiments, the grip 22 may have a variable outer diameter. For example, the grip 22 may have a generally hour glass shape such that a central outer diameter 56 is smaller than end outer diameters 58, 60. In this manner, the smaller portion of the grip 22 may better conform to the hands of the users, thereby enhancing the user experience during operation of the therapeutic wand 10.

Furthermore, as illustrated in FIG. 2, the tip 12 and the head 16 are both generally rounded. As will be described below, because the tip 12 and the head 16 are designed to be placed against the skin (e.g., at the face, at the neck, etc.), the rounded tip 12 and head 16 enhance comfort and reduce the pressure felt by the user during operation. However, in certain embodiments, the tip 12 and the head 16 may have flat, polygonal, or pointed shapes. For example, the tip 12 may include a fine point, similar to a needle, to concentrate the force applied by the therapeutic wand 10. In this manner, different tips 12 and/or heads 16 may be utilized to provide a range of treatment options.

Figure 3:
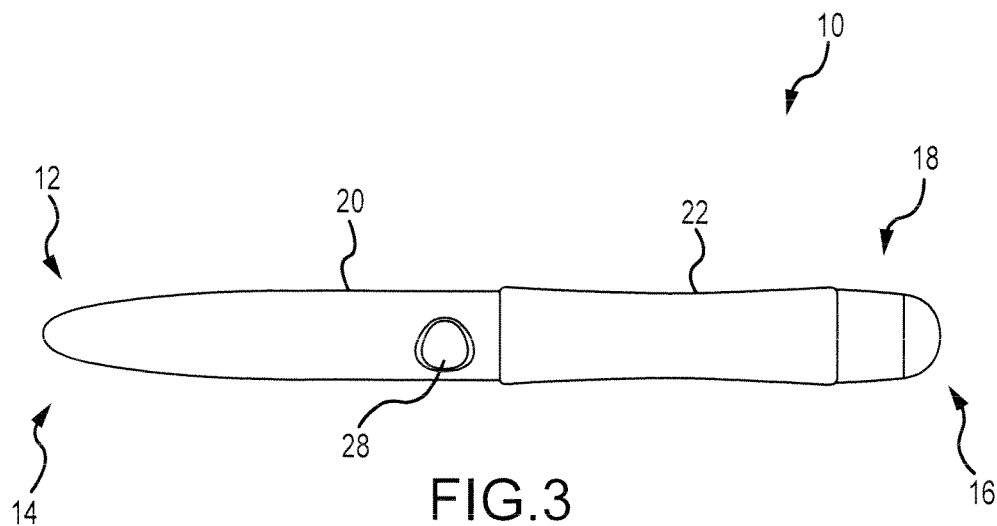
FIG. 3 is a side elevational view of an embodiment of a therapeutic wand having a tactile switch, in accordance with embodiments of the present disclosure.

FIG. 3 is a side elevational view of the therapeutic wand 10, wherein the switch 28 is a tactile switch. As described above, the therapeutic wand 10 includes the body 20 positioned between the tip 12 at the first end 14 and the head 16 at the second end 18. Moreover, the grip 22 is arranged proximate the head 16 to facilitate movement and manipulation of the therapeutic wand 10 by the user. In the illustrated embodiment, the switch 28 is arranged on the body 20 and is a tactile switch that is activated by the user pressing against it. Moreover, the user pressing against the switch 28 a second time deactivates the therapeutic wand 10. As shown, the switch 28 is arranged on the body 20 to prevent inadvertent activation and/or deactivation during use. For example, because the user holds the therapeutic wand 10 at the grip 22, the switch 28 remains away from the portion the user is holding onto. As a result, inadvertent activation and/or deactivation are reduced, thereby improving the user experience. However, it should be appreciated that, in certain embodiments, the switch 28 may be positioned at different locations along the therapeutic wand 10. For example, the switch 28 can be at and/or proximate the tip 12, at/or proximate the head 16, or any other suitable position along the therapeutic wand 10.

Figure 4:
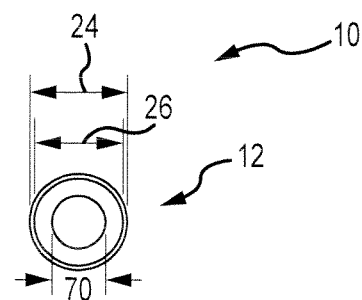
FIG. 4 is a top plan view of the therapeutic wand of FIG. 1 having a tip, in accordance with embodiments of the present disclosure.

FIG. 4 is a bottom plan view of the therapeutic wand 10 illustrating the generally circular, spherical surface of the tip 12. As will be described below, in certain embodiments, the tip 12 is brought into contact with a skin surface, for example, on the face, and an electric motor within the therapeutic wand 10 generates massaging, vibrational pulses that are transferred to the skin. Because the tip 12 has a smooth, hemispherical shape, the vibrations are distributed over a larger surface area, thereby reducing the pressure on the skin, while still providing massaging pulses to improve circulation and lymph drainage. It should be understood that, in certain embodiments, the tip 12 may be flat, arcuate, elliptical, or pointed to provide different benefits. For example, the tip 12 may be pointed to more closely simulate acupuncture and to direct the force of the therapeutic wand 10 over a smaller area, thereby concentrating and increasing the pressure applied to the area. In the illustrated embodiment, the tip 12 has a smaller tip outer diameter 70 than the grip outer diameter 24 or the body outer diameter 26. But, in certain embodiments, the tip 12 may be larger than or equal to the grip outer diameter 24 and/or the body outer diameter 26.

Figure 5:
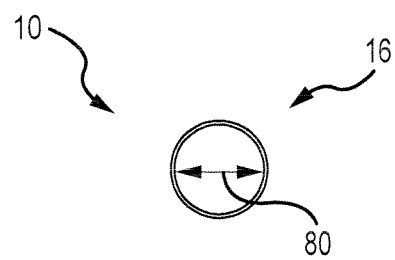
FIG. 5 is a bottom plan view of the therapeutic wand of FIG. 1 having a head, in accordance with embodiments of the present disclosure.

FIG. 5 is a top plan view of the therapeutic wand 10 illustrating the generally circular, spherical surface of the head 16. As described above, in certain embodiments, the head 16 may be utilized to massage and/or rub the skin to stimulate blood flow and/or provide therapeutic properties believed to be related to one or more precious stones, semi-precious stones, man-made stones, minerals, or metals positioned within and/or acting as the head 16. For example, in certain embodiments, the head 16 may be rose quartz, jade, sapphire, mother of pearl, or any other stone, metal, or mineral (e.g., precious, semi-precious, or man-made) believed by practitioners of alternative medicine to be related to health, beauty, and/or wellness. As described above, in certain embodiments, the head 16 may be removable, thereby allowing the user to change the head 16 (and, in certain embodiments, the precious stone, semi-precious stone, man-made stone, mineral, or metal) to accommodate a variety of health, wellness, and beauty needs. In the illustrated embodiment, the head outer diameter 80 is substantially equal to the grip outer diameter 24. As a result, the grip 22 and the body 20 are obscured in the view shown in FIG. 5. However, in other embodiments, the head outer diameter 80 may be equal to or smaller than the grip outer diameter 24 and/or the body outer diameter 26.

Figure 6:
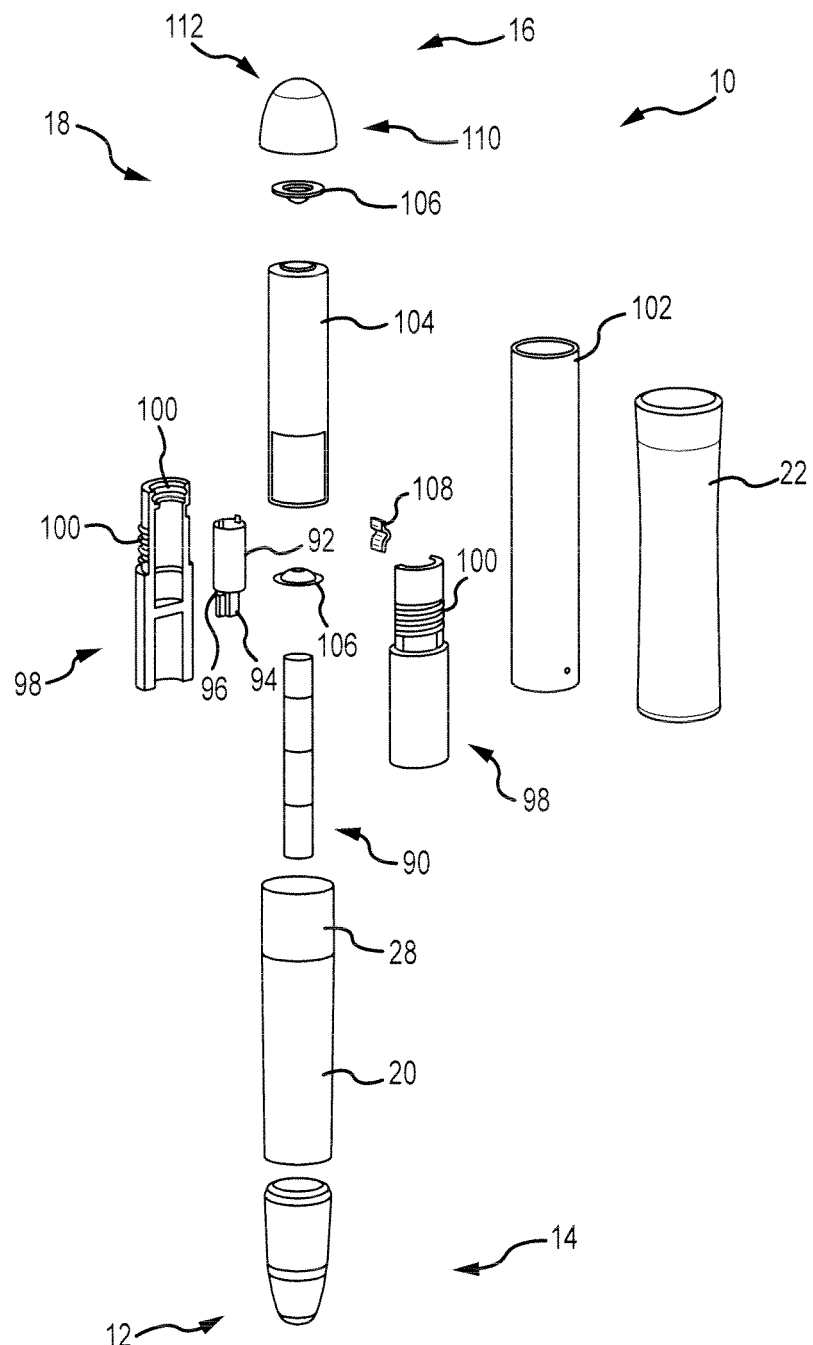
FIG. 6 is an exploded assembly view of the therapeutic wand of FIG. 1, in accordance with embodiments of the present disclosure.

FIG. 6 is an exploded assembly view of the therapeutic wand 10 in an embodiment where the therapeutic wand 10 includes the twist switch 28. As shown, the tip 12 is arranged at the first end 14 and is positioned to couple to the body 20.

As will be described below, in certain embodiments, the tip 12 includes a cavity to receive a conductor or semi-conductor, for example, germanium, to enhance the conductive properties of a magnet 90 arranged to be positioned within the body 20. In certain embodiments, as illustrated in FIG. 6, the magnet 90 is an electromagnet having a cylindrical shape positioned within the body 20. The magnet 90 is placed within the body 20 and closely positioned to a motor 92. In the illustrated embodiment, the motor 92 (e.g., a vibration motor) includes an off-center weight 94. Movement of the off-center weight 94 generates vibrations as a shaft 96 rotates. These vibrations are transferred to the tip 12, thereby generating a massaging effect when positioned against the skin. In certain embodiments, the motor 92 may have a number of settings that enable increased vibrational forces via changes in the rotational speed of the shaft 96. For example, the motor 92 may have three settings corresponding to a light, medium, or high level of vibrations. As will be described below, different settings may be used when the therapeutic wand 10 is utilized on different areas of the body. For example, the light setting may be used when the therapeutic wand 10 is positioned close to the eyes. However, the medium or heavy setting may be used when the therapeutic wand 10 is used on the cheeks or neck. In this manner, different levels of activation may be set by the user to generate an improved physical appearance of the skin. As described above, the massaging effect is transferred to the skin to improve circulation and/or lymph drainage to thereby improve the physical appearance of the skin.

The illustrated embodiment also includes an internal housing 98 arranged to fit within the body 20 and secure the motor 92 in place. As shown, the internal housing 98 includes a threaded connection 100 to facilitate coupling to the grip 22. For example, in the illustrated embodiment, the grip 22 includes an interior structure 102, in the form of a substantially cylindrical tube, to facilitate connection to the internal housing 98, and thereby the body 20 of the therapeutic wand 10. In certain embodiments, a battery 104 is utilized as a power source for the motor 92. The therapeutic wand 10 includes contacts 106 to transmit power from the battery 104 to the motor 92 when the switch 28 is activated. For example, rotation of the switch 28 may move a battery clip 108 into a position to transmit electrical energy from the battery 104 to the motor 92. Moreover, as described above, in certain embodiments the motor 92 may have multiple settings (e.g., light, medium, high, etc.). As a result, the user may rotate the switch 28 additional times to change the setting. For example, a single rotation may correspond to the light setting, two rotations may correspond to the medium setting, and three rotations may correspond to the high setting. Similarly, one, two, or three touches to a tactile switch may correspond to the light, medium, and heavy settings, respectively.

Furthermore, the head 16 is arranged at the second end 18 of the therapeutic wand 10 and connected to the grip 22. In the illustrated embodiment, the head 16 is positioned within an upper housing 110. For example, in certain embodiments, the upper housing 110 includes a cavity 112 for receiving the head 16. As described above, the 16 may be a precious stone, semi-precious stone, man-made stone, mineral, or metal utilized for properties believed to be transmitted from the precious stone, semi-precious stone, man-made stone, mineral, or metal by practitioners of alternative medicine. Accordingly, in certain embodiments, the head 16 may be removable and/or replaceable so as to enable the user to change the head 16 to receive a variety of benefits. For example, the head 16 may be connected to the upper housing 110 by a press fit, thread, clip, or any other suitable means of connection. In this manner, the therapeutic wand 10 can be assembled for use by a user and, in certain embodiments, for disassembly by a user to replace components (e.g., the battery 104, the tip 12, the head 16). As will be appreciated, the tolerances and fit of the various components may be particularly selected so as to reduce auditory noise and/or vibration in certain portions of the therapeutic wand 10. For example, the connection between the interior housing 98 and the grip 22 may be arranged so as to reduce the vibration generated by the motor 92 at the grip 22, thereby enhancing the comfort felt by the user utilizing the therapeutic wand 10. Moreover, in certain embodiments, additional components may be incorporated into the therapeutic wand 10. For example, the therapeutic wand 10 may include a printed circuit board, various sensors, indicators, speeds, levels of vibration, and the like.

Figure 7:
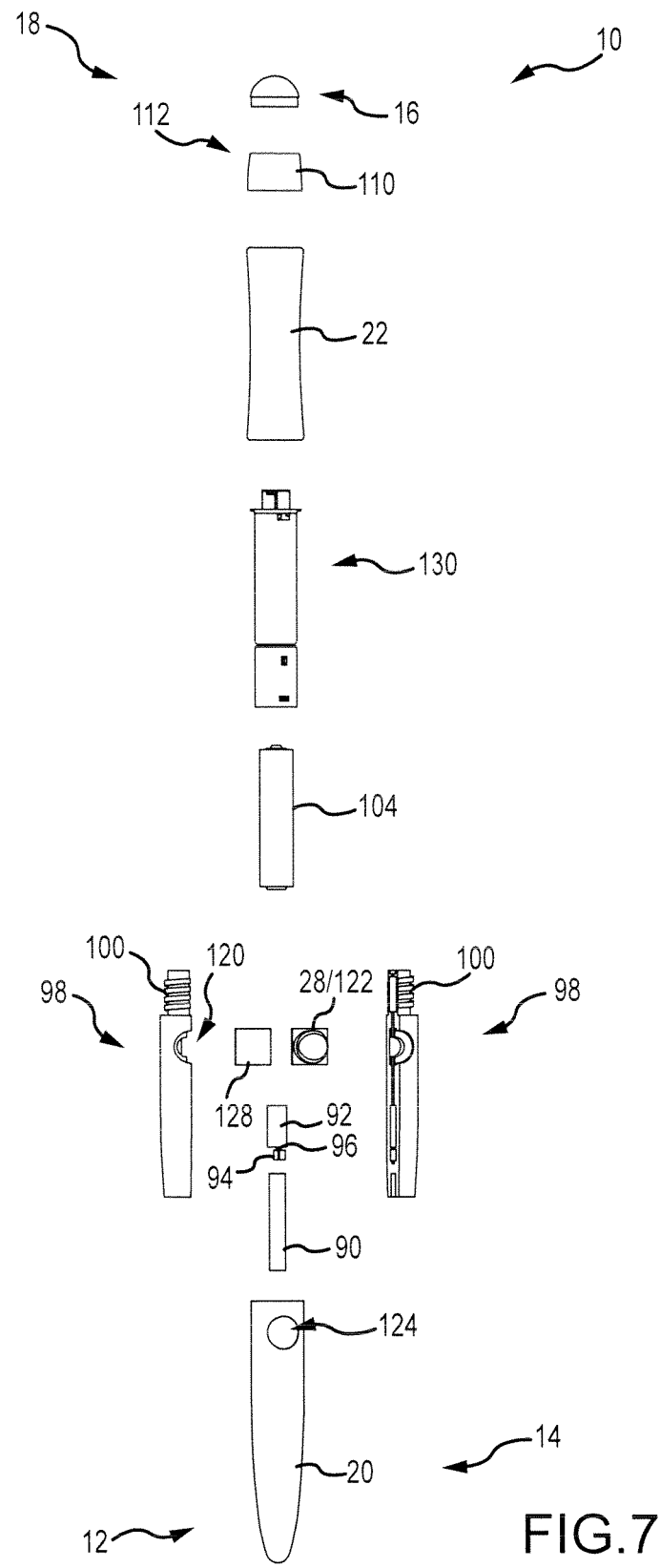
FIG. 7 is an exploded assembly view of the therapeutic wand of FIG. 3, in accordance with embodiments of the present disclosure.

FIG. 7 is an exploded assembly view of the therapeutic wand 10 having the tactile switch 28. As described above, the therapeutic wand 10 is formed from components connected together in a substantially side-by-side, co-axial arrangement to form a substantially cylindrical, pen-shaped device. In the illustrated embodiment, the tip 12 is arranged at the first end 14 and includes a cavity (not pictured) for germanium, or some other conductive or semi-conductive material, to enhance and/or stimulate the electrical field generated by the magnet 90. In certain embodiments, the magnet 90 is an electromagnet that generates a magnetic field via an electrical coupling to the motor 92 and/or the battery 104. The magnet 90 is closely arranged to the motor 92. As described above, the motor 92 generates vibrations through the tip 12 via rotation of the off-center weight 94 about the shaft 96. As described above, in certain embodiments, the motor 92 may have multiple intensity settings.

In the illustrated embodiment, the internal housing 98 includes an aperture 120 that enables a tact switch 122 to extend outwardly from the internal housing 98 and through a hole 124 formed through the body 20. The tact switch 122 enables the motor 92 to be turned on or off, by facilitating an electrical connection between the motor 92 and the battery 104, thereby enabling the user to control operation of the therapeutic wand 10. For example, the therapeutic wand 10 may be powered by a single battery 104 (e.g., an AAA battery, an AA battery, etc.) Furthermore, as described above, in certain embodiments the motor 92 may have multiple settings that are activated by contacting the tact switch 122 multiple times (e.g., one push for low level, two pushes for medium level, and three pushes for high level). In certain embodiments, the tact switch 122 is electrically connected to a printed circuit board 128. As will be described below, in certain embodiments, the printed circuit board 128 may be a processor that provides feedback to a user during operation. For example, the printed circuit board 128 may be connected to an indicator, such as a buzzer or light that provides a notice (e.g., a ring or a flash) to the user after certain time durations have passed.

In the illustrated embodiment, the therapeutic wand 10 includes a battery housing 130 arranged to receive and support the battery 104. For example, the battery housing may be threadingly connected to the body 20 via the illustrated threaded connection 100. However, in other embodiments, the battery housing 130 may be clipped to the body 20 or otherwise connected to the body 20. As shown, the grip 22 is arranged to slide over the battery housing 130 to provide an ergonomic and comfortable grip for the user. Moreover, as described above, the upper housing 110 may be connected to the grip 22 and the head 16 via threaded connections, push connections, clips, or the like. In this manner, the therapeutic wand 10 may be assembly for operation by a user. Moreover, it should be appreciated that other components, such as indicators and sensors, may be arranged within or external to the therapeutic wand 10. Additionally, as will be understood by those skilled in the art, a dampening lining, such as formed by silicone or thermoplastic elastomer (TPE), may be positioned within the interior housing of the wand 10 to dampen sound and/or vibration occurring from the vibration or other operating characteristics of the wand 10. For example, more specifically, a dampening lining as described could be positioned along the shaft of the wand to enhance sound and/or vibration dampening.

Figure 8A:
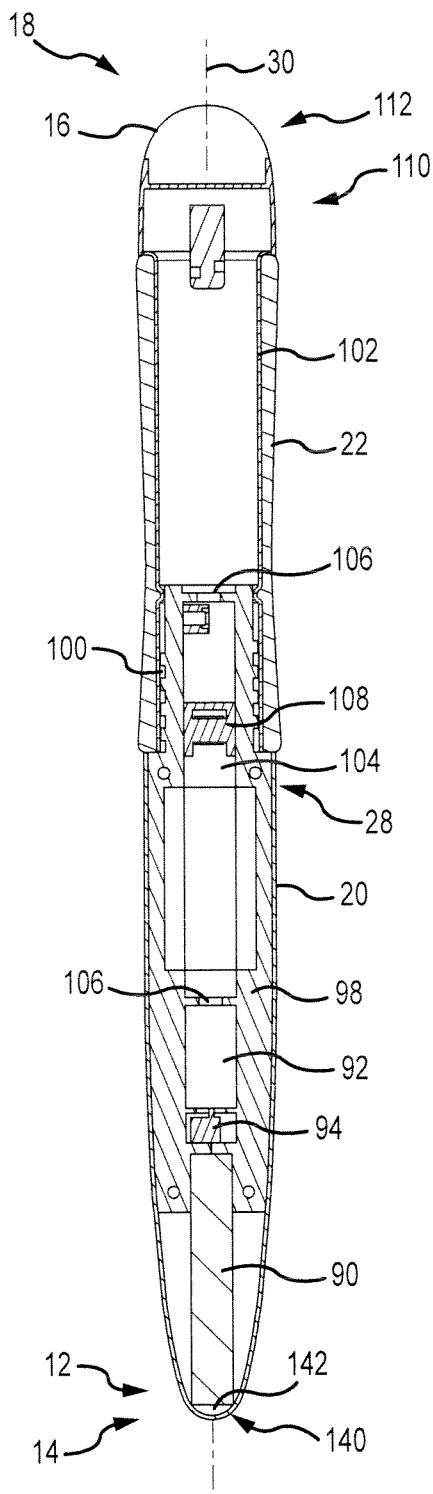
FIG. 8A is a cross-sectional side view, taken along line 8-8, of the therapeutic wand of FIG. 1, in accordance with embodiments of the present disclosure.
Figure 8B:
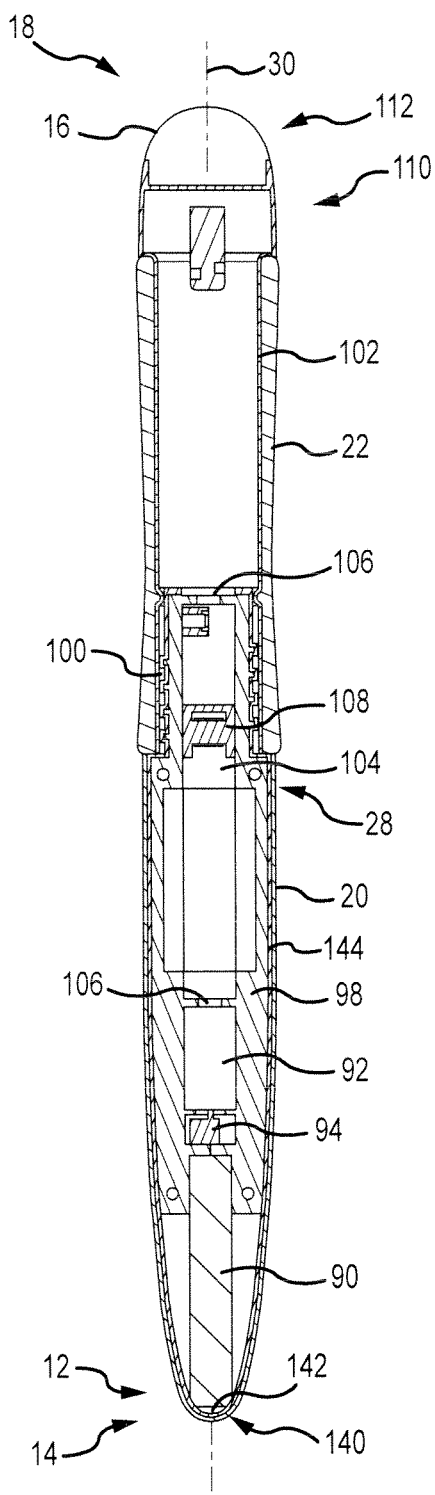
FIG. 8B is a sectional, taken along line 8-8, of an embodiment of the therapeutic wand of FIG. 1, in accordance with embodiments of the present disclosure.

FIGS. 8A and 8B are cross-sectional side views, taken along line 8-8, of the therapeutic wand 10. In the illustrated embodiment, the therapeutic wand 10 includes the twist switch 28. However, it should be appreciated that, in other embodiments, the therapeutic wand 10 may include the tact switch 122. As illustrated, the tip 12, the body 20, the grip 22, and the head 16 are arranged substantially co-axially along the longitudinal axis 30. The tip 12 includes a cavity 140 for housing a conductor or semi-conductor 142, such as germanium, to enhance the magnetic field generated by the magnet 90. For example, in certain embodiments, the body 20 is formed from surgical stainless steel, and therefore, is not magnetic. However, by providing the magnet 90 and the semi-conductor 142, the therapeutic wand 10 may provide the benefits practitioners of alternative medicine believe to be associated with magnet therapy.

As described above, the magnet 90 is closely arranged with the motor 92, which is in electrical communication with the battery 104 to generate vibrational pulses at the tip 12. In this manner, when the tip 12 is placed against the skin, the skin receives a massaging, vibrational energy that can stimulate blood flow and circulation and/or lymph drainage to enhance the appearance of the skin. Moreover, in the illustrated embodiment, the threaded connection 100 couples the internal housing 98 to the internal structure 102. The grip 22 is arranged circumferentially about the internal structure 102 such that the user will contact the grip 22 when holding the therapeutic wand 10 for use. Moreover, as illustrated, the upper housing 110 is connected to the interior structure 102 via a clip or press fit. In addition, the head 16 is arranged within the cavity 112 in the upper housing 110, thereby enabling the precious stone, semi-precious stone, man-made stone, mineral, or metal to be incorporated into the therapeutic wand 10.

The above-described dampening lining 144 is illustrated extending around the body 20 in FIG. 8B. In certain embodiments, the dampening lining 144 is a flexible, resilient material that absorbs at least a portion of vibration or sound emanating from the therapeutic wand 10. For instance, in embodiments the motor 92 may generate vibrations that are transmitted to the tip 12 via the magnet 90 and off-center weight 94. The dampening lining 144 may reduce the tactile sensation of the vibrations at the grip 22 while enabling transmission of the vibration to the tip 12. In this manner, the therapeutic benefits of the vibration may be realized while enhancing the comfort of using the wand 10 for the user. It should be appreciated that while the illustrated embodiment includes the dampening lining 144 around the body 20, in other embodiments the dampening lining 144 may be arranged around a particular element. For instance, as will be shown in FIG. 9, the dampening lining 144 may be arranged at least partially around the motor 92. Accordingly, it should be appreciated that the location of the dampening lining 144 may be particularly selected based on the desired dampening effects.

Figure 9:
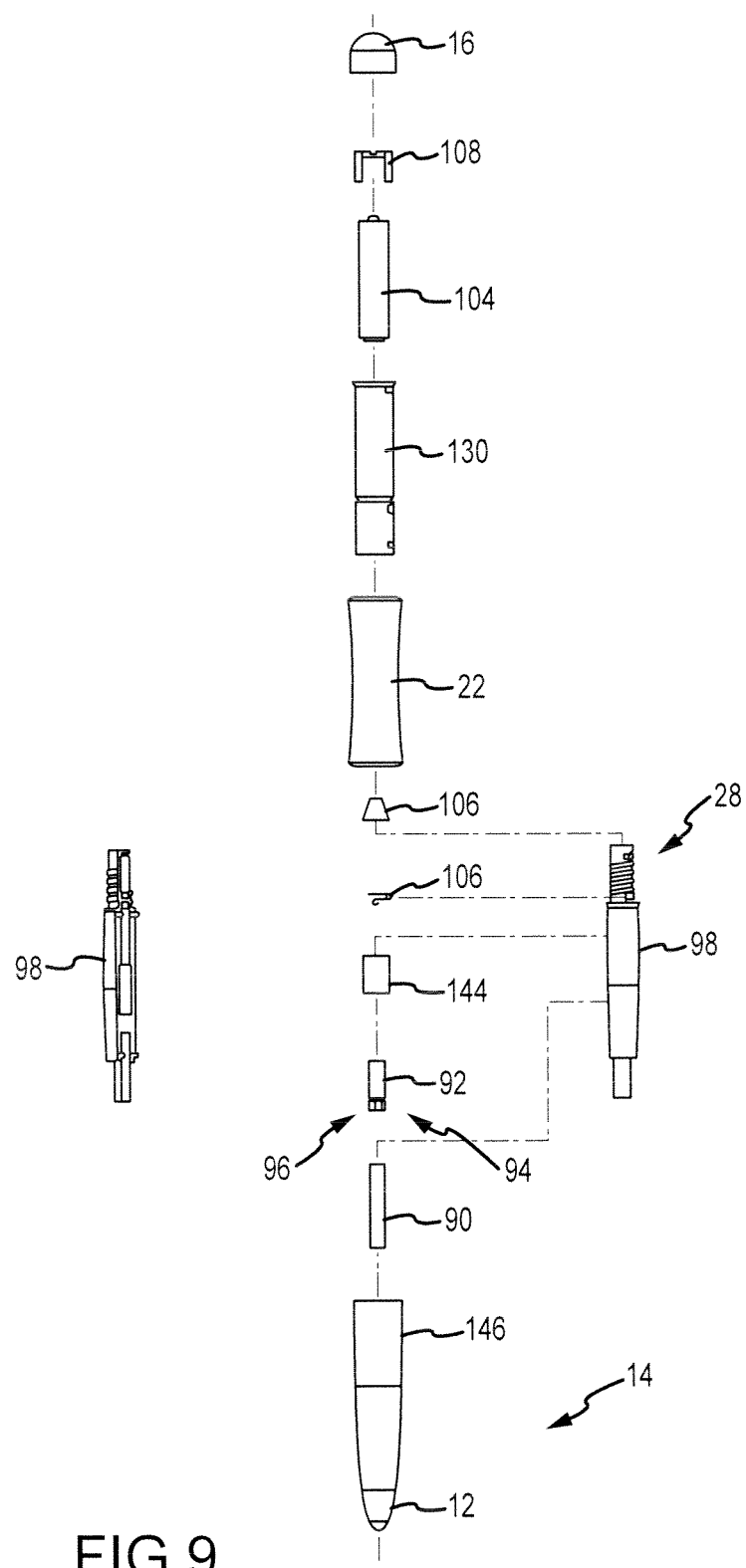
FIG. 9 is an exploded assembly view of an embodiment of a therapeutic wand, in accordance with embodiments of the present disclosure.

FIG. 9 is an exploded assembly view of the therapeutic wand 10 having the twist switch 28. As described above, the therapeutic wand 10 is formed from components connected together in a substantially side-by-side, co-axial arrangement to form a substantially cylindrical, pen-shaped device. In the illustrated embodiment, the tip 12 is arranged at the first end 14 and includes a cavity (not pictured) for germanium, or some other conductive or semi-conductive material, to enhance and/or stimulate the electrical field generated by the magnet 90. In certain embodiments, the magnet 90 is an electromagnet that generates a magnetic field via an electrical coupling to the motor 92 and/or the battery 104. The magnet 90 is closely arranged to the motor 92. As described above, the motor 92 generates vibrations through the tip 12 via rotation of the off-center weight 94 about the shaft 96. As described above, in certain embodiments, the motor 92 may have multiple intensity settings.

In the illustrated embodiment, a lower housing 146 is connected to the tip 12 and positioned to receive the magnet 90 and the internal housing 98. The internal housing 98 has been split in the illustrated embodiment for clarity to reveal one or more spaces to receive and store internal components of the wand 10. Furthermore, the switch 28 is integrated into the internal housing 98. However, it should be appreciated that in other embodiments the switch 28 may be arranged at a different position. In the embodiment illustrated in FIG. 9, the dampening lining 144 is in the form of a dampening sleeve that is arranged around the motor 92. In operation, vibration produced by the motor 92 may be transferred to the dampening lining 144 and the energy may be absorbed instead of transferred to the grip 22. In certain embodiments, the contacts 106 are arranged within the internal housing 98 to facilitate forming an electrical contact between the motor 92 and the battery 104. As described above, it should be appreciated that the battery 104 refers to any device that can store and/or transmit electrical enemy. In the embodiment illustrated in FIG. 9, the battery 104 may be arranged within the battery housing 130 and secured via the battery clip 108. For instance, the battery 104 may slide into the battery housing 130, which may be arranged to extend through the grip 22 toward the contacts 106 to transmit electrical energy from the battery 104 to the motor 92. The head 16 may be utilized to secure the battery 104 within the wand 10. In this matter, the wand 10 may be structured to transmit vibrational and/or magnetic energy to the user.

Figure 10:
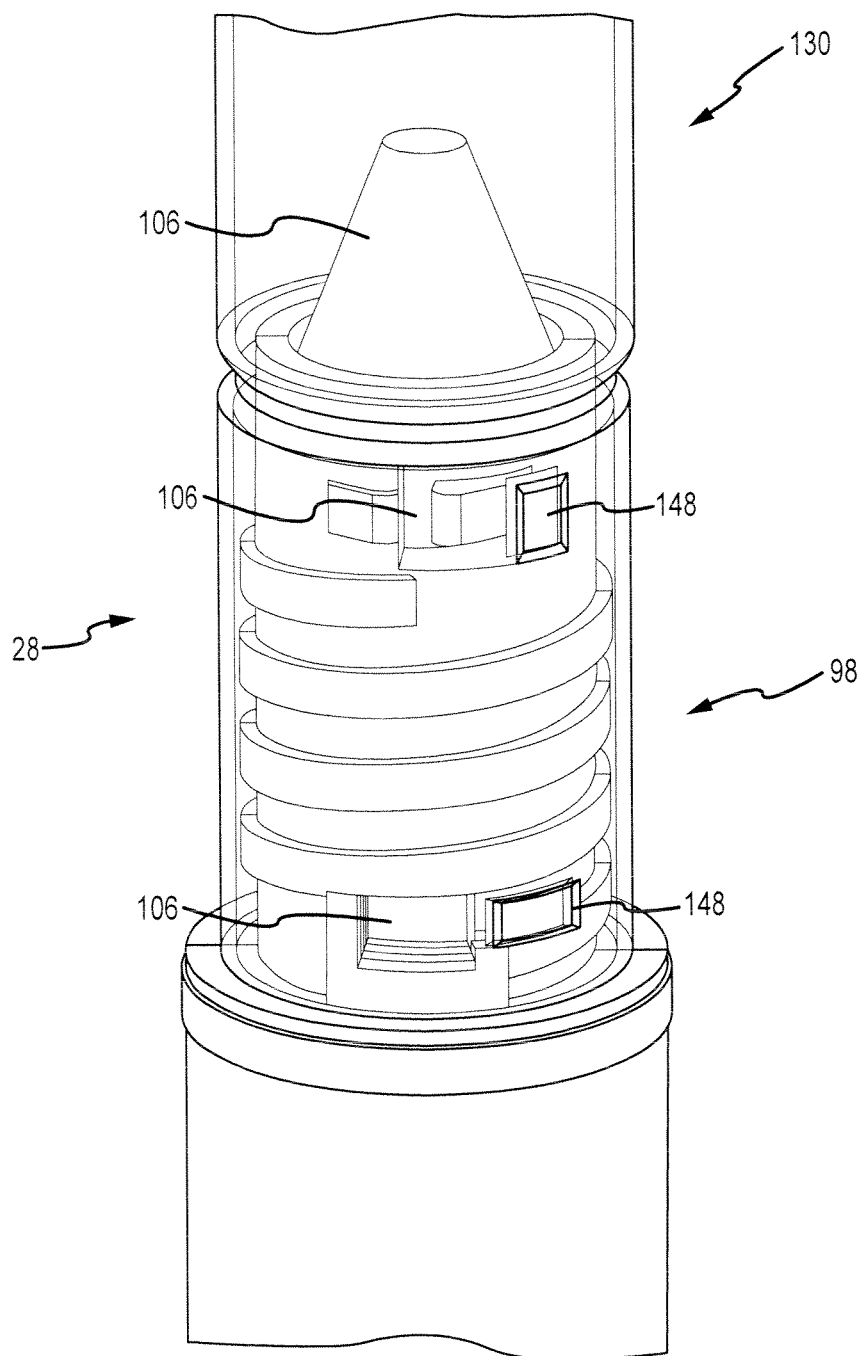
FIG. 10 is an isometric view of an embodiment of a twist switch in an off position, in accordance with embodiments of the present disclosure.

FIG. 10 is an isometric view of an embodiment of the switch 28. In the illustrated embodiment, the switch 28 is a twist switch that moves between an on position and an off position via a twisting and/or rotational movement. In the illustrated embodiment, the switch 28 is positioned below the battery housing 130 which houses the battery 104 (not shown) to transmit electrical energy via the contact 106. As shown, a junction 148 is positioned circumferentially spaced apart from the contact 106 extending through the switch 28. As such, there is no transference of electrical energy to the motor 92 and the wand 10 is in the office position. As will be described below, rotating the junction 148 into position with the contact 106 facilitates transmission of electrical energy to the motor 92.

In certain embodiments, the switch 28 is integrated into the internal housing 98, the battery housing 130, the lower housing 146, the grip 22, or any other suitable position on the wand 10. In the embodiment illustrated in FIG. 10, the switch 28 may be covered the grip 22 (not shown) and integrated into the internal housing 98. As such, the grip 22 may facilitate rotation of the switch 28 between the on position and the off position.

Figure 11:
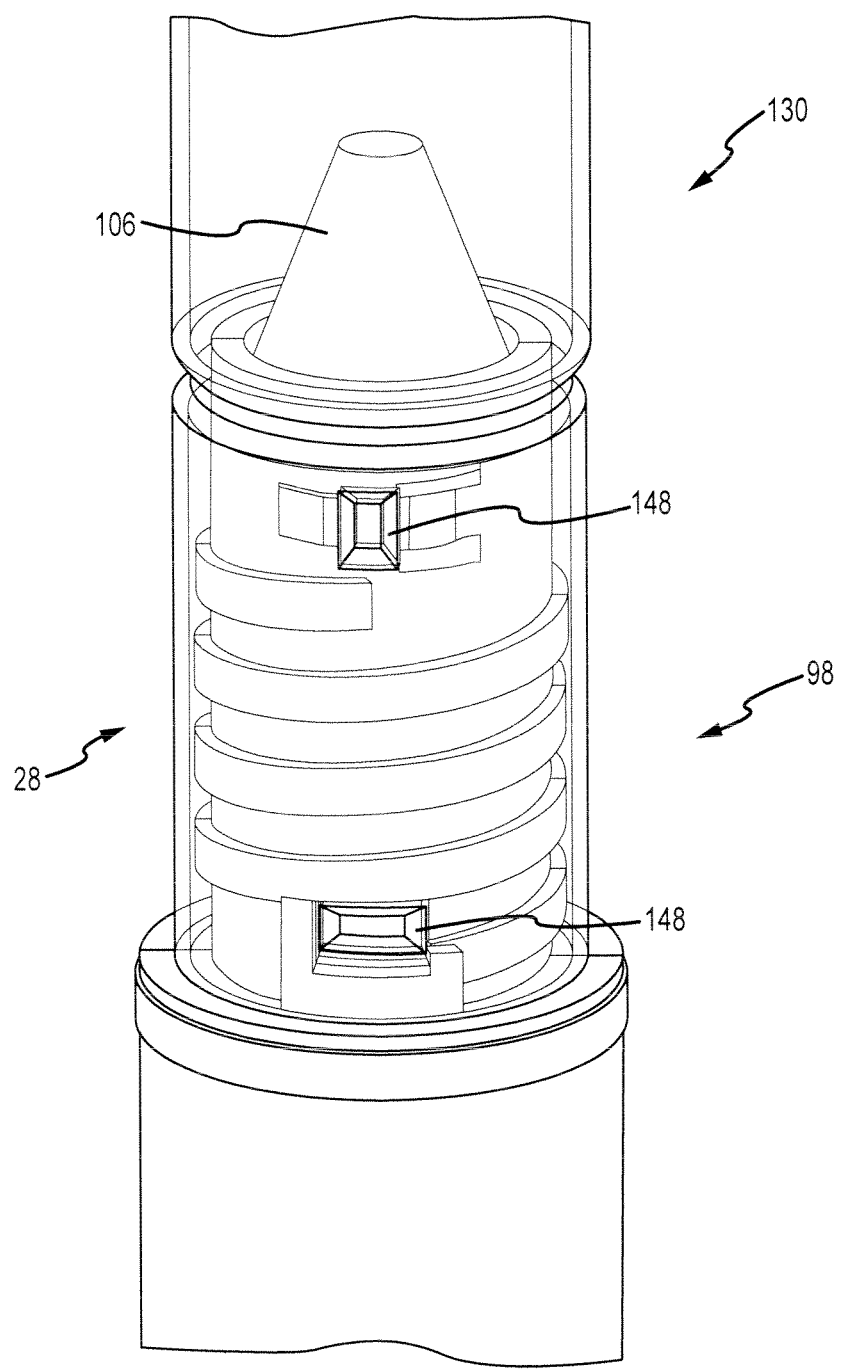
FIG. 11 is an isometric view of an embodiment of a twist switch in an on position, in accordance with embodiments of the present disclosure.

FIG. 11 is an isometric view of an embodiment of the switch 28 arranged in the on position. As described above, the switch 28 may be rotatable such that the junctions 148 move circumferentially and engage the contacts 106 to transmit electrical energy from the battery 104 to the motor 92. In certain embodiments, the junctions 148 may be substantially locked into place such that the user does not continue to rotate the switch 28 to maintain the on position. In other words, the junctions 148 may include a detent to snap into position to hold the switch 28 in the on position until an external force, for example from the user, is applied to the wand 10. In certain embodiments, the junction 148 may extend inwardly toward the contact 106 such that once the junction 148 and the contact 106 are aligned the junction 148 is arranged within a void or opening proximate the contact 106 to facilitate the transfer of electrical energy. In this manner, the wand 10 may be arranged in the on position.

Figure 12:
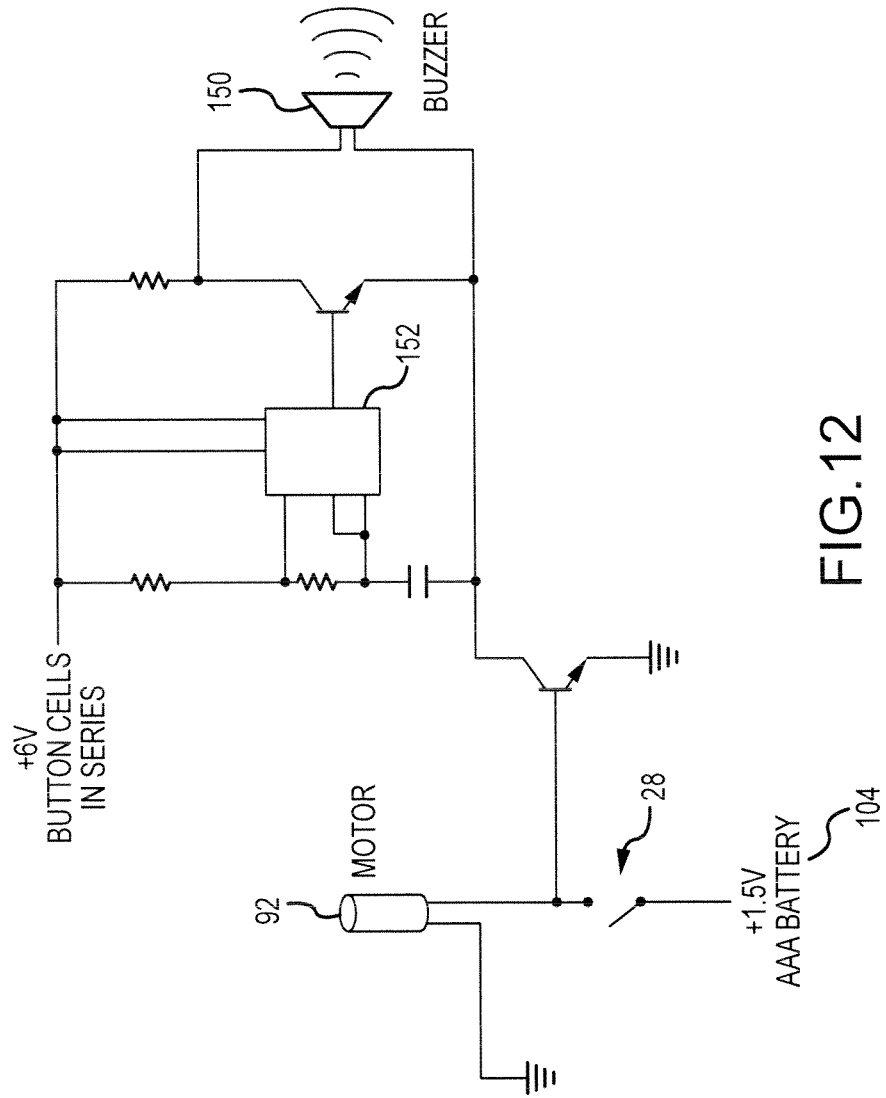
FIG. 12 is a schematic circuit diagram of an embodiment of an indicator positioned within the therapeutic wand of FIG. 1, in accordance with embodiments of the present disclosure.

FIG. 12 is an embodiment of a schematic circuit diagram positioned within the therapeutic wand 10. In the illustrated embodiment, the schematic circuit diagram may be referred to as a timer circuit. In certain embodiments, the therapeutic wand 10 includes an indicator 150 electrically connected to the battery 104 to transmit a notification to the user. For example, in certain embodiments, improved results may be generated by holding the therapeutic wand 10 at acupressure points for a predetermined period of time. Therefore, the therapeutic wand 10 can include the indicator 150, such as a buzzer or visual indictor, to notify the user when the predetermined period of time has passed. In this manner, the user may experience enhanced operation of the therapeutic wand 10 and improved results.

As illustrated, the motor 92 is electrically connected to the battery 104 via the switch 28. In the illustrated embodiment, the switch 28 is in the open position, and therefore, no electrical energy flows from the battery 104 to the motor 92. That is, the electrical coupling between the motor 92 and the battery 104 is broken by the switch 28. Moreover, the battery 104 is also electrically connected to a timer circuit 152. The timer circuit 152, in certain embodiments, is an integrated chip, for example a 555 timer IC, as known by one skilled in the art. In certain embodiments, the timer circuit 152 may operate in a monostable mode or a stable mode that includes a timer that resets after a predetermined period of time. At each interval where the timer reaches the predetermined period of time, the timer circuit 152 may transmit an electrical signal (e.g., a command), to the indictor 150. In the illustrated embodiment, the indicator 150 is a buzzer. Upon receipt of the signal from the timer circuit 152, the buzzer 150 transmits an auditory alarm to the user, thereby indicating that the predetermined period of time has passed and that the user should move the therapeutic wand 10 to a different acupressure point. As shown, the circuit may include various other components, such as resistors, capacitors, switches, and the like to facilitate operation. Moreover, as indicated above, in certain embodiments the indicator 150 may include a light (e.g., a light emitting diode), an auditory alarm (e.g., the buzzer), tactile feedback (e.g., a vibrator), or the like. However, it should be understood that in certain embodiments, the therapeutic wand 10 includes a digital circuit, such as a microcontroller operated by the printed circuit board 128.

Figure 13:
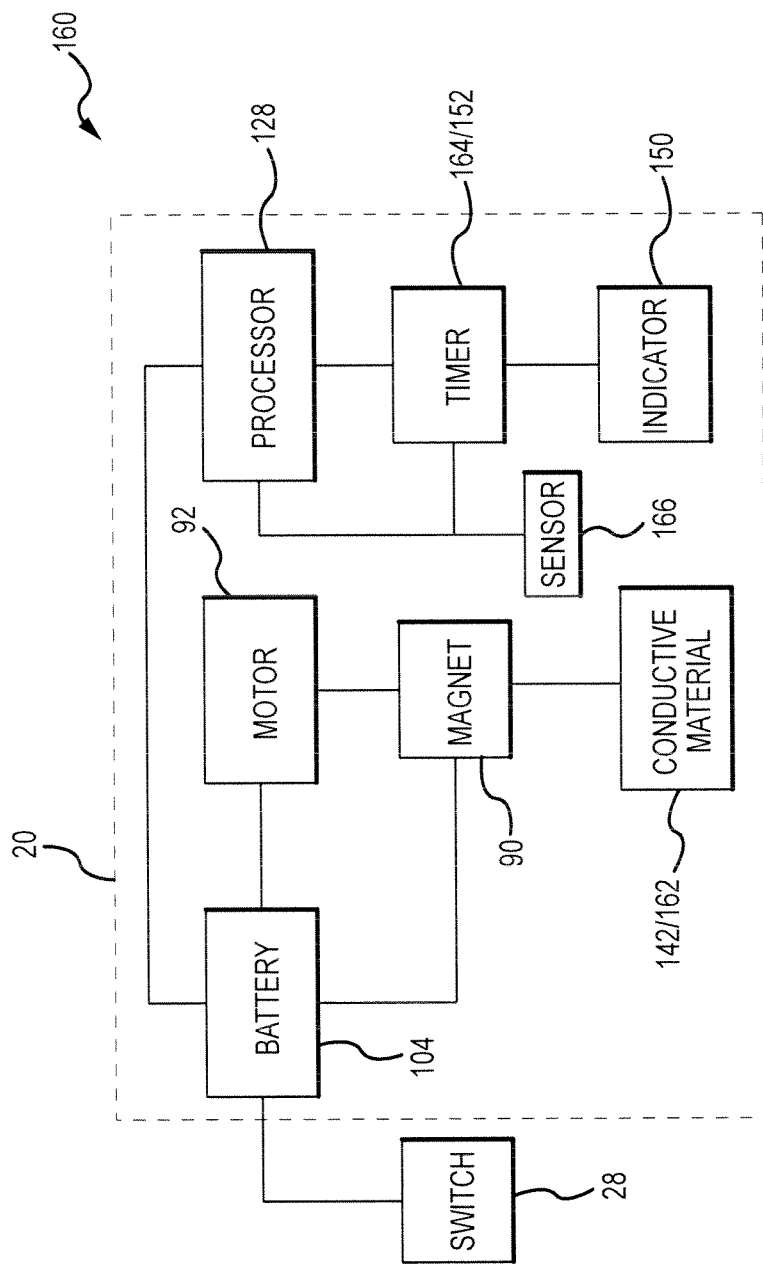
FIG. 13 is a schematic block diagram of an embodiment of a circuit and control system for the therapeutic wand of FIG. 1, in accordance with embodiments of the present disclosure.

FIG. 13 is a schematic block diagram of an embodiment of a circuit and control system for the therapeutic wand 10. As described above, the therapeutic wand 10 may include circuitry to control operation of the therapeutic wand 10 and to provide indications to users regarding operation and functionality of the therapeutic wand 10. In the illustrated embodiment, a control system 160 is arranged, at least partially, within the body 20 of the therapeutic wand 10. In the illustrated embodiment, the switch 28 is communicatively connected to the battery 104. For example, the switch 28 can activate the flow of electrical energy from the battery 104 to the motor 92, thereby producing vibrational energy within the therapeutic wand 10. For example, in certain embodiments, engaging the switch 28 one or more times may activate the motor 92 and adjust the intensity level of the motor. Moreover, in the illustrated embodiment, the battery 104 is electrically connected to the magnet 90. As described above, in certain embodiments, the magnet 90 is an electromagnet that generates an electric field at least partially due to the energy received from the battery 104. Furthermore, as shown in FIG. 13, the magnet 90 may be connected to the conductive material 162 (e.g., conductor or semi-conductor). In certain embodiments, the conductive material 162 is germanium. However, in other embodiments, any conductive or semi-conductive material 142 may also be utilized.

In the illustrated embodiment, the control system 160 includes the printed circuit board 128, in the form of a processor (e.g., a microprocessor, a microcontroller). In certain embodiments, the processor includes one or more non-transistory, machine readable memories (e.g., ROM, RAM, Flash, etc.) for storing machine-readable instructions. Moreover, the printed circuit board 128 is communicatively connected to a timer 164 (e.g., timer circuit 152). As described above, users may receive enhanced benefits from using the therapeutic wand 10 for predetermined time periods. Accordingly, the timer 164 may be used to keep track of the time the user is operating the therapeutic wand 10. The timer 164 may relay the information to the printed circuit board 128 for processing and further use. In the illustrated embodiment, the timer 164 is connected to a sensor 166. For example, in certain embodiments, the sensor 166 may be arranged in the tip 12 and detect compression and/or contact of the tip 12 to a surface, such as skin. Upon activation of the sensor 166, the timer 164 may activate. However, it should be appreciated that, in other embodiments, the sensor 166 may be omitted or incorporated into another portion of the therapeutic wand 10. For example, the sensor 166 may be a button or switch arranged on the body 20 that the user contacts and holds during use of the therapeutic wand 10. In this manner, the timer 164 may be activated without positioning the sensor 166 in the tip 12 of the therapeutic wand 10. Furthermore, in the illustrated embodiment, the timer 164, and the printed circuit board 128 via the timer 164, is communicatively connected to the indicator 150. As described above, when the timer 164 determines that a predetermined time period has passed (e.g., 5 seconds, 10 seconds, 15 seconds, etc.), the timer 164 and/or the printed circuit board 128 may transmit a signal to the indicator 150 to transmit an indication to the user. For example, in certain embodiments, the indication may be a buzzer that produces an auditory indication to the user. Moreover, in certain embodiments, the indication may be a light that produces a visual indication to the user. It should be appreciated that any type of reasonable indication (e.g., visual, auditory, tactile, etc.) may be utilized by the therapeutic wand 10. In this manner, the control system 160 may guide the user during operation of the therapeutic wand 10.

Figure 14:
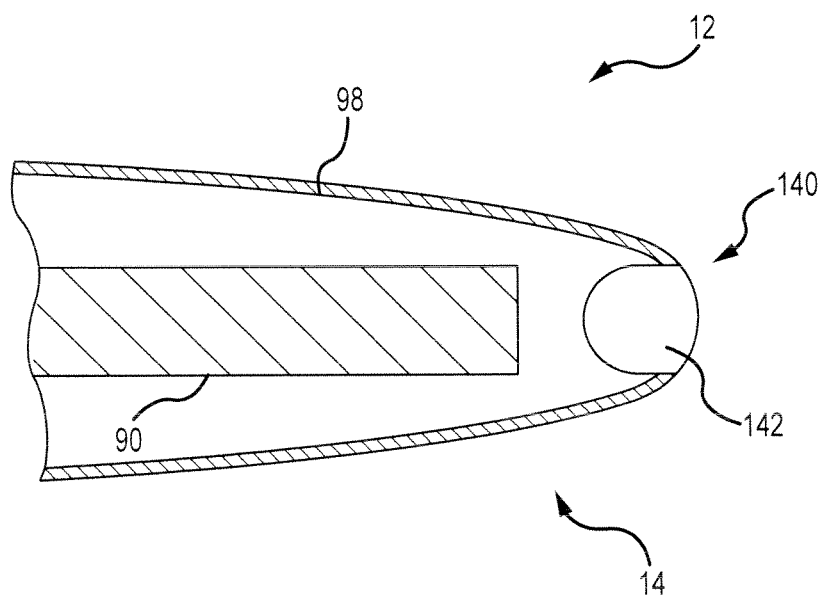
FIG. 14 is a partial cross-sectional side view, taken along line 14-14, of an embodiment of a tip of the therapeutic wand of FIG. 1, in accordance with embodiments of the present disclosure.

FIG. 14 is a partial cross-sectional side view, taken along line 14-14, of an embodiment of the tip 12. As described above, the tip 12 is arranged at the first end 14 of the therapeutic wand 10 for contact with a surface, e.g., the skin of a human face, to transmit vibrational impulses generated by the motor 92 to acupressure points. In the illustrated embodiment, the tip 12 includes the cavity 140 for receiving the conductor or semi-conductor 142. Moreover, as illustrated, the magnet 90 is closely positioned to the conductor or semi-conductor 142 to thereby enhance the effects of the magnetic field generated by the magnet 90.

Figure 15:
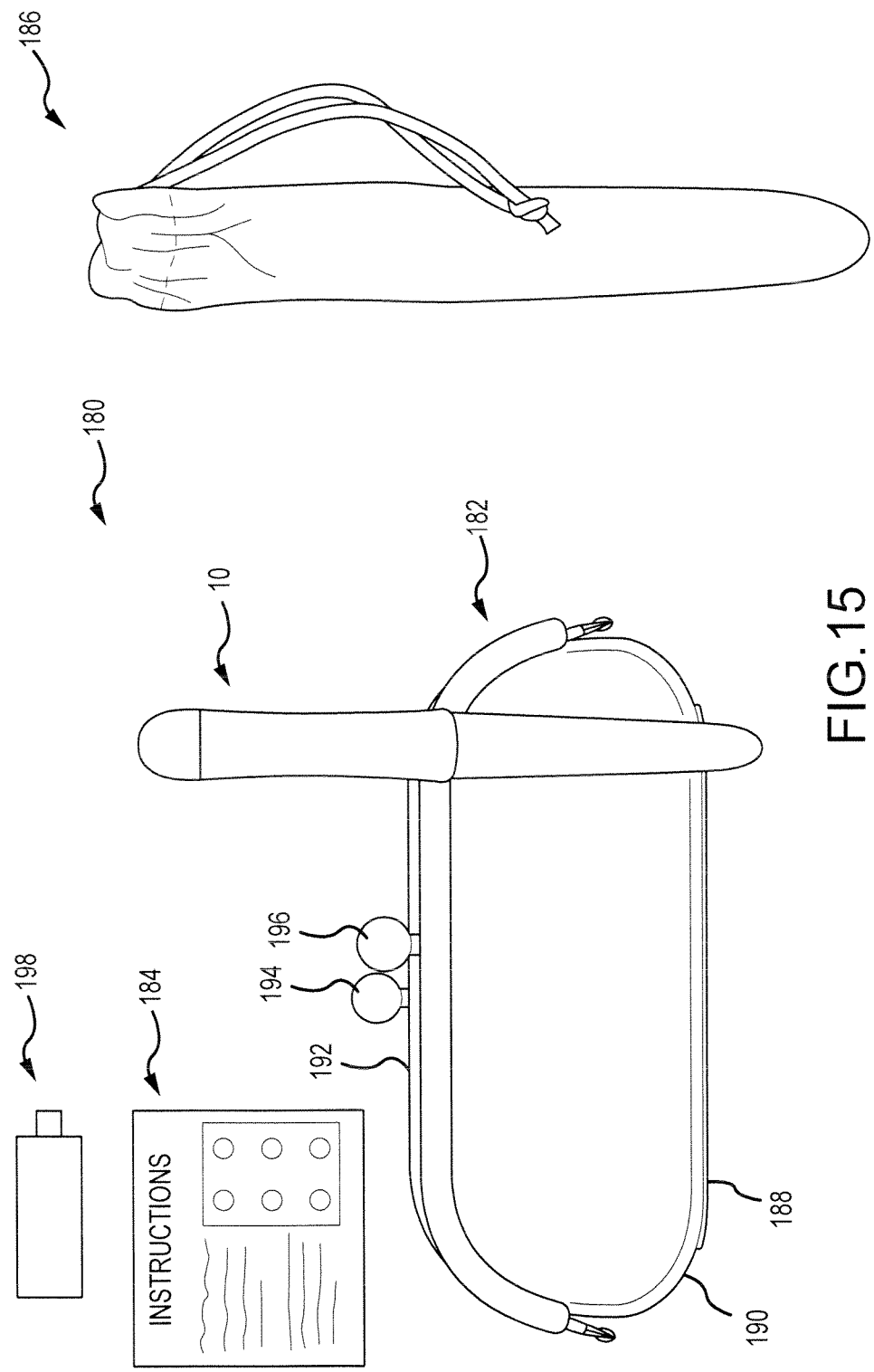
FIG. 15 is a front perspective view of a therapeutic wand kit including a therapeutic wand, an instruction booklet, a covering, and a container, in accordance with embodiments of the present disclosure.

FIG. 15 is a front perspective view of a therapeutic wand kit 180. In the illustrated embodiment, the therapeutic wand kit 180 includes the therapeutic wand 10, a container 182, an instruction booklet 184, and a covering 186. In the illustrated embodiment, the container 182 is a case having a generally clam-shell appearance. As will be understood by those skilled in the art, the container 182 also can be an enhanced eco-friendly container such as a hard bamboo-type case (e.g., that opens in a clam, bag, or other arrangement thereby to allow insertion and removal of a wand 10, as well as some or all of other elements of a therapeutic wand kit 180) that has eco-friendly characteristics and yet provides some protection for a wand 10 when positioned therein. Other types of eco-friendly material and structures for a container also can be used as will be understood by those skilled in the art. As shown in FIG. 15, the container 182 is connected at a seam 188 and positioned to move between an open and closed position via movement of a first body portion 190 and a second body portion 192 about the seam 188. For example, the body portions 190, 192 include opening features 194, 196 arranged opposite the seam 188 and extruding outwardly from the body portions 190, 192. In operation, the user can engage the opening features 194, 196 to open the container 182. It should be appreciated that in certain embodiments the covering 186 provides additional protective properties to the wand 10.

Moreover, as shown in FIG. 15, the kit 180 includes the therapeutic wand 10, as described in detail above. The therapeutic wand 10 is sized such that it fits within the container 182, thereby securing the therapeutic wand 10 from damage and facilitating easy transportation of the therapeutic wand 10. For example, the therapeutic wand 10 may be positioned within one or more compartments within the container 182. Furthermore, the covering 186 is sized to cover and secure the therapeutic wand 10 when the therapeutic wand 10 is in the container 182. For example, in certain embodiments, the covering 186 is a bag formed from a soft material (e.g., silk, microfiber, cotton, etc.) to cushion the therapeutic wand 10 from humps or jolts. Moreover, the covering 186 provides a secondary device for moving the therapeutic wand 10 between locations when the container 182 may be too large or bulky (e.g., within carry-on luggage). It should be appreciate that the covering 186 may be manufactured to be form-fitting with the therapeutic wand 10 (e.g., tightly aligned with the shape of the therapeutic wand 10) and/or larger to provide additional room and area around the therapeutic wand 10. Furthermore, in certain embodiments, the covering 186 may not include a closure mechanism (e.g., string, hook and loop fasteners, etc.) and may resemble a sleeve with an open ending.

Furthermore, in the illustrated embodiment, the kit 180 includes the instruction booklet 184 for providing instructions to the user for operating the therapeutic wand 10. For example, the instruction booklet 184 may include step-by-step instructions, and photographs, for performing a variety of exercises and techniques with the therapeutic wand 10 to generate an improved physical appearance. In addition, while the illustrated embodiment includes the instruction booklet 184 as a print out, in other embodiments, the instruction booklet 184 may be a computer program that can be downloaded on a personal electronic device (e.g., a smart phone, a tablet, a computer, etc.) that includes text, images, and video to instruct the user how to properly utilize the therapeutic wand 10 via an included memory stick 198 (e.g., a USB drive, an SD card, or the like). Moreover, the booklet 184 may not be a book, but rather a sheet or pamphlet. As known by one skilled in the art, the memory stick 198 (e.g., a flash drive) is a data storage device with an integrated universal serial bus (USB) and a small printed circuit board. For example, the instruction booklet 184 and/or the memory stick 198 may include a link to a website, and in some embodiments, a password or access code, to enable the user to download the instructions. Furthermore, in certain embodiments, the instructions may be operable on a personal electronic device via a program (e.g., an app) that can be downloaded and accessed on the personal electronic device. For example, the user may download the program and execute the program on the personal electronic device to obtain instructions, track usage statistics, or the like. Thereafter, the user will have convenient access to the instructions, for example, if they do not have the instruction booklet 184 readily available. Furthermore, in certain embodiments, the memory stick 198 may be provided in lieu of or in addition to the instruction booklet 184. Moreover, in certain embodiments, the kit 180 may also include replacement parts, such as extra tips 12, heads 16, grips 22, or the like to enable the user to change the functionality and/or appearance of the therapeutic wand 10.

Figure 16:
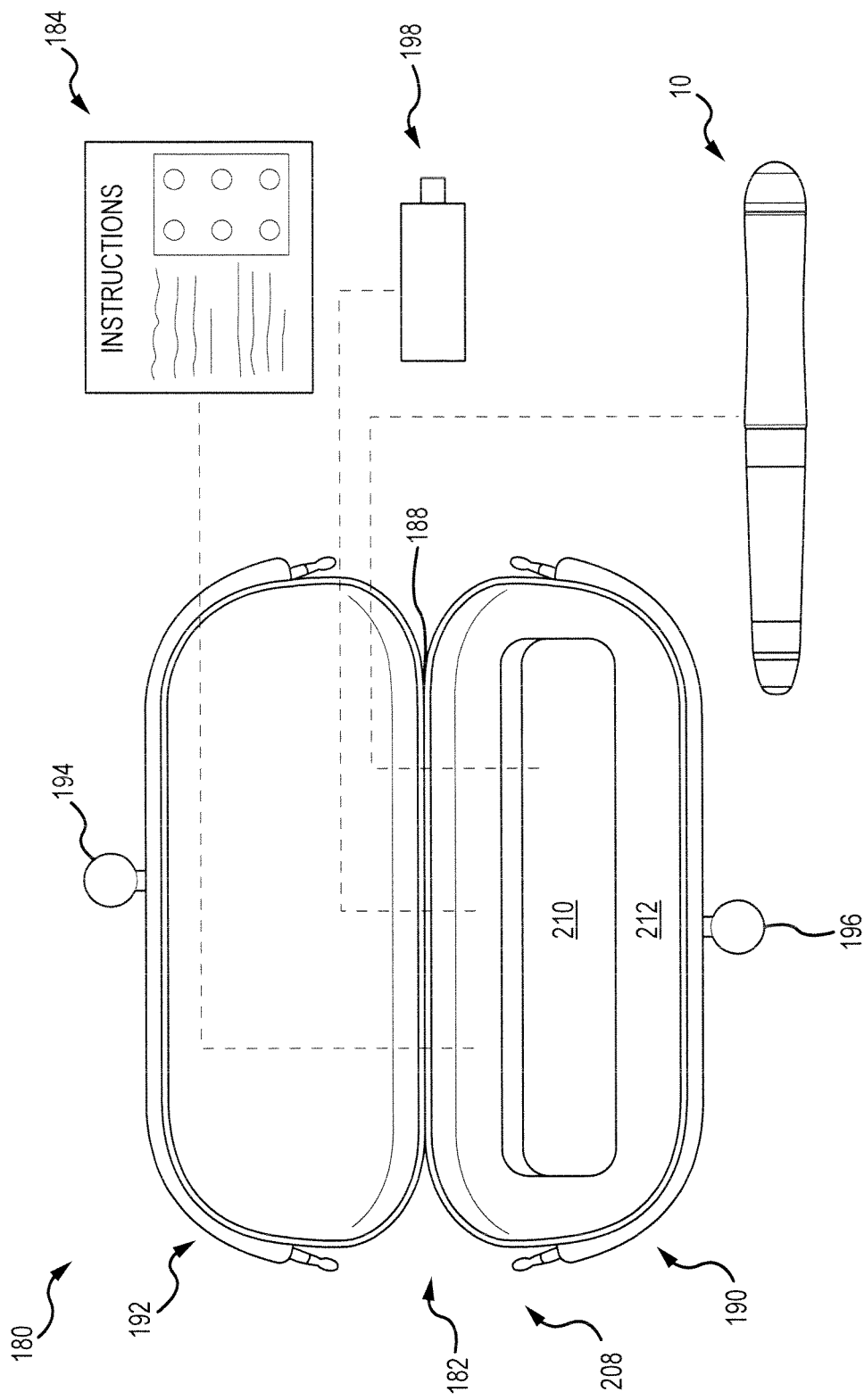
FIG. 16 is an exploded front perspective view of an assembly of the therapeutic wand kit of FIG. 12, in accordance with embodiments of the present disclosure.

FIG. 16 is an exploded front perspective view of an assembly of the therapeutic wand kit 180. As illustrated, the body portions 190, 192 are arranged to lay substantially flat, while connected at the seam 188. Moreover, the container 182 includes one or more compartments 208 for receiving the other components of the kit 180. In the illustrated embodiment, the container 182 includes a bed 210 for receiving the therapeutic wand 10 is visible and arranged to receive the therapeutic wand 10. In certain embodiments, the bed 210 is indented into the container 182, such that a surface 212 surrounds and defines the bed 210. The bed 210 may be shaped to receive the therapeutic wand 10 with a tight or secure fit, thereby preventing shifting and/or movement of the therapeutic wand 10 when the therapeutic wand 10 is positioned within the container 182. Moreover, the bed 210 may be sized to accommodate the therapeutic wand 10 positioned within the covering 186, thereby providing additional security to the therapeutic wand 10.

As illustrated by the lead lines, the container 182 is arranged to receive the therapeutic wand 10, the instruction booklet 184, and the memory stick 198 in a uniform and organized way, thereby enhancing the user experience as the therapeutic wand 10 is removed from the container 182. For example, the user may open the container 182 to see the instruction booklet 184 arranged neatly beside the therapeutic wand 10. Moreover, the secure placement of the therapeutic wand 10 within the container 182 may provide assurances to the user that the therapeutic wand 10 was securely shipped and will operate properly. Furthermore, in certain embodiments, the covering 186 is also positioned within the container 182. For example, the covering 186 may be arranged around the therapeutic wand 10. However, in the illustrated embodiment, the covering 186 has been omitted for clarity. Accordingly, the design and functionality of the container 182, as part of the kit 180, may enhance the user experience related to the therapeutic wand 10.

Figure 17:
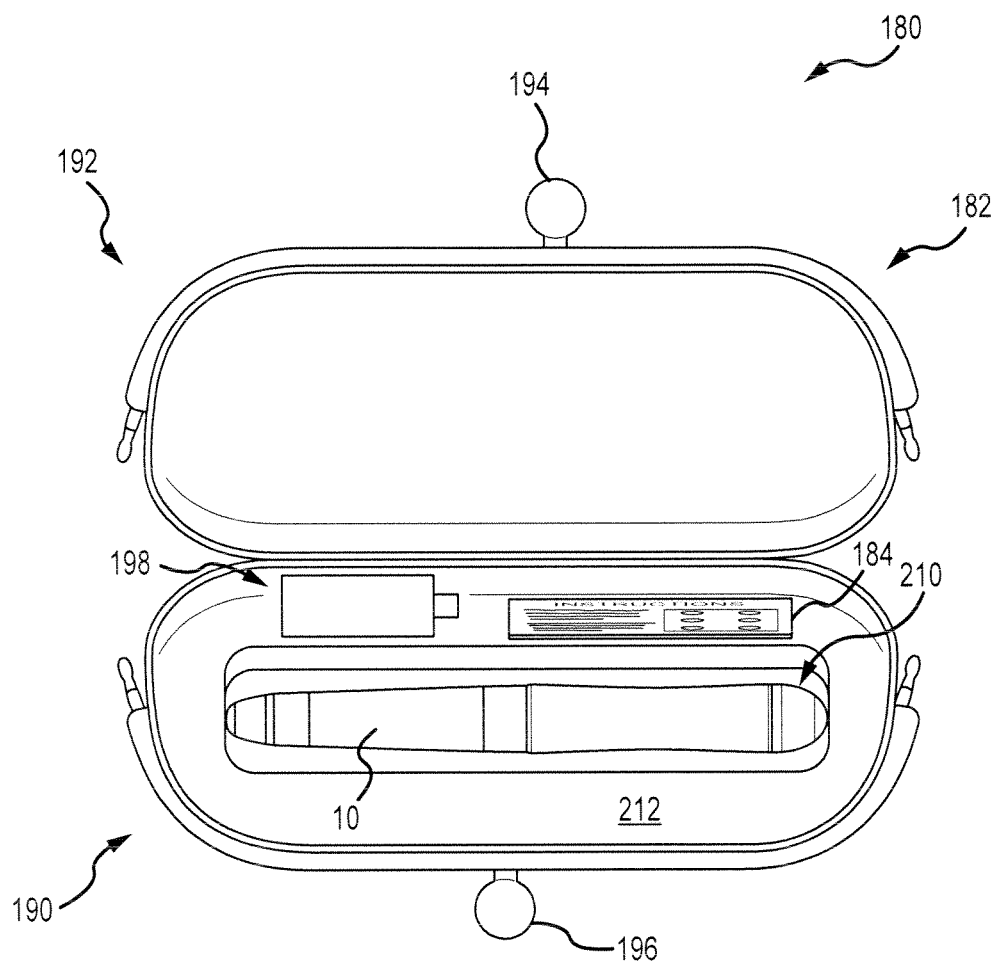
FIG. 17 is a top plan view of the therapeutic wand kit of FIG. 15, in accordance with embodiments of the present disclosure.

FIG. 17 is a top plan view of the therapeutic wand kit 180. As illustrated, the therapeutic wand 10 is positioned within the container 182 in a secure position within the bed 210. However, it should be appreciated that, in certain embodiments, the container 182 may not include the bed 210. Furthermore, in the illustrated embodiment, the covering 186 has been omitted to clarify the position of the therapeutic wand 10 within the bed 210 (e.g., compartment). However, it should be appreciated that the bed 210 (e.g., compartment) may be sized to facilitate inclusion of the covering 186 about the therapeutic wand 10. Moreover, as illustrated, the instruction booklet 184 is arranged beside the therapeutic wand kit 180. In the illustrated embodiment, the instruction booklet 184 is arranged beside the memory stick 198. However, in other embodiments, the instruction booklet 184 may be arranged below the therapeutic wand 10 or on top of the therapeutic wand 10. Moreover, in certain embodiments, the instruction booklet 184 may be omitted in favor of the memory stick 198. In this manner, an attractive presentation is shown to the user when they first open the container 182 to utilize the therapeutic wand 10.

Figure 18:
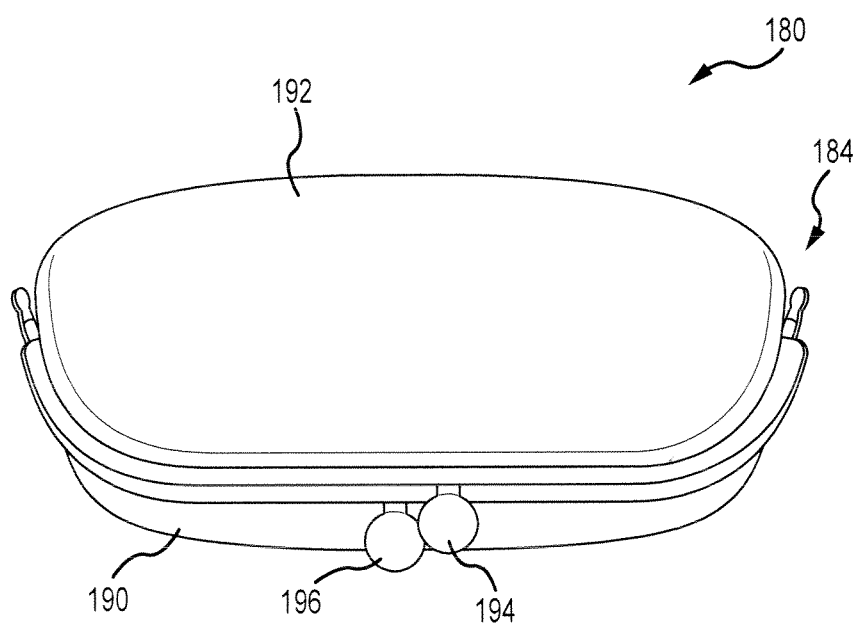
FIG. 18 is a front perspective view of the container of the therapeutic wand kit of FIG. 12, in accordance with embodiments of the present disclosure.

FIG. 18 is a front perspective view of the container 182 of the therapeutic wand kit 180. As described above, in the illustrated embodiment, the container 182 is in the form of a clam shell type case having body portions 190, 192 connected together at a seam 188. In certain embodiments, the container 182 may be formed from a soft, gel-like, malleable material to account for external forces. Moreover, forming the container 182 from a soft material may facilitate absorption of external forces and provide easier packing or storage options for users. Furthermore, the gel-like material can be color coordinated to provide an aesthetically pleasing appearance for users, thereby further enhancing the user experience associated with the therapeutic wand kit 180.

Figure 19:
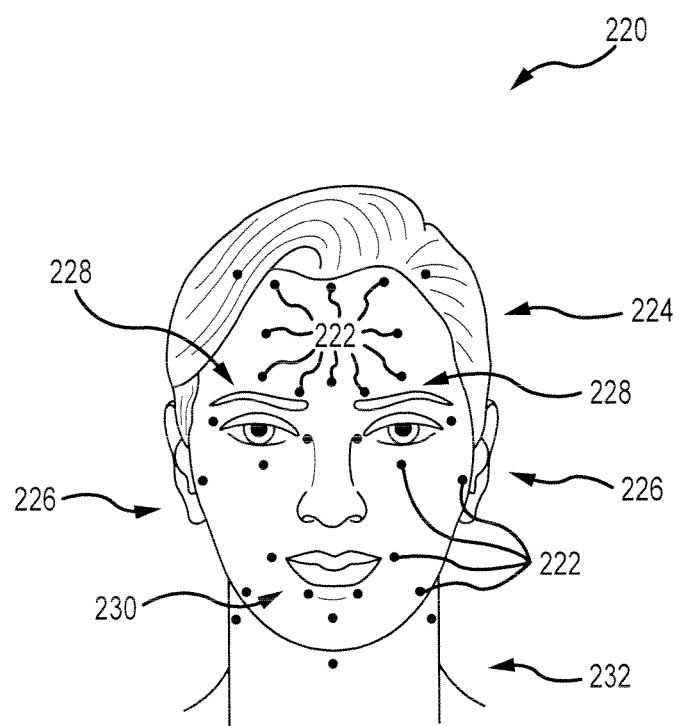
FIG. 19 is a front schematic view of a human face having acupressure points, in accordance with embodiments of the present disclosure.

FIG. 19 is a front schematic view of an embodiment of a human face 220 having acupressure points 222. As described above, practitioners of traditional Chinese medicine and/or alternative medicine believe that acupressure points 222 are arranged at locations along the human body that can help channel life force energy and bring health, beauty, and wellness to persons. In practice, the acupressure points 222 are stimulated via external pressures applied to the skin, for example, via a finger or other device. As illustrated, the acupressure points 222 are positioned along various locations on the human face 220, such as the forehead 224, the cheeks 226, around the eyes 228, around the mouth 230, and around the neck 232. As will be described below, in certain embodiments, the therapeutic wand 10 may be utilized to apply pressure to one or more of the acupressure points in a predetermined, guided series in order to generate an improved physical appearance of the skin. Moreover, massaging pressure and/or force may be applied by the head 16 of the therapeutic wand 10 to further generate an improved physical appearance of the skin.

Figure 20:
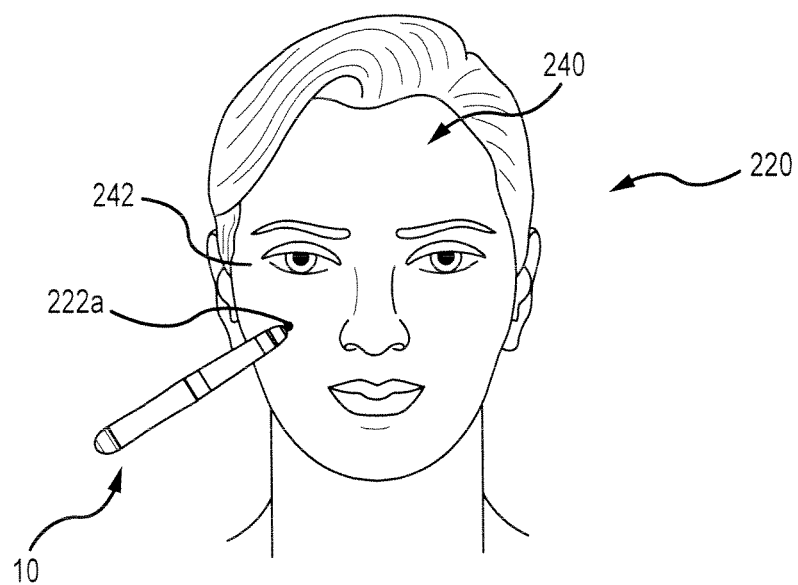
FIG. 20 is a schematic view of an embodiment of a therapeutic wand positioned at an acupressure point on a human face, in accordance with embodiments of the present disclosure.

FIG. 20 is a schematic view of an embodiment of the therapeutic wand 10 positioned at the acupressure point 222a on the human face 220. As described above, the acupressure point 222a may correspond to one or more meridians that facilitate the movement and flow of life energy through the body, thereby promoting health, beauty, and wellness. Moreover, in certain embodiments, the acupressure point 222a may correspond to areas of skin 240 where certain signs of aging, such as wrinkles, sagging, color imbalances, and the like, are commonly present. For example, as humans age, wrinkles may form due to glycation, sun damage, smoking, poor hydration, and the like. The acupressure point 222a, when stimulated by the therapeutic wand 10, may improve and/or lessen the appearance of these signs of aging due to the massaging effects generated by the motor 92, the magnetic field generated by the magnet 90, and/or the precious stone, semi-precious stone, man-made stone, mineral, or metal in the head 16. As illustrated, the therapeutic wand 10 is positioned proximate the acupressure point 222a such that the tip 12 is placed into contact with a surface 242 of the skin 240 on the human face 220. From there, the user can apply gentle pressure to the skin 240 as the motor 92 generates vibrations that are transmitted from the tip 12 to the skin 240, thereby stimulating the acupressure point 222a. In this manner, at-home treatment of skin imperfections (e.g., lines, wrinkles, discolorations, sagging, etc.) may be performed using the therapeutic wand 10.

Figure 21:
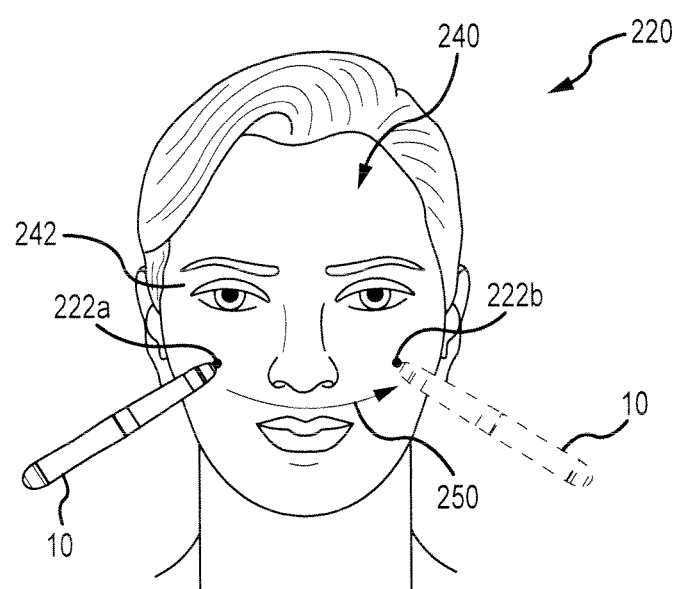
FIG. 21 is a schematic view of an embodiment of a tip of the therapeutic wand of FIG. 1 massaging an acupressure point on a human face, in accordance with embodiments of the present disclosure.

FIG. 21 is a schematic view of an embodiment of the tip 12 of the therapeutic wand 10 moving between acupressure points 222a, 222b on the human face 220. As described above, the tip 12 is brought into contact with the surface 242 of the skin 240 at or near the acupressure point 222a to transmit vibrational energy and/or magnetic energy from the therapeutic wand 10 to the skin 240. In this manner, the skin 240 may be stimulated, thereby promoting blood circulation and/or lymph drainage. Moreover, stimulating the acupressure point 222a is believed by practitioners of traditional Chinese medicine and/or alternative medicine to promote health, beauty, and wellness. As described above, in certain embodiments, the user may move the therapeutic wand 10 along a predetermined path in order to stimulate a variety of acupressure points 222 to generate an improved physical appearance of the skin 240. In the illustrated embodiment, the arrow 250 represents movement of the therapeutic wand 10 between the acupressure points 222a and 222b. In certain embodiments, the movement may be done in a sweeping motion, while maintaining contact with the skin 240. However, in certain embodiments, the tip 12 may be removed from the skin 240 proximate the acupressure point 222a and then positioned at the acupressure point 222b without contacting intermediate skin between the acupressure points 222a, 222b. As will be described in detail below, in certain embodiments, the instruction booklet 184 may include a regimen providing a path of acupressure points 222 to stimulate in order to promote health, beauty, and wellness to improve the physical appearance of the skin 240.

Figure 22:
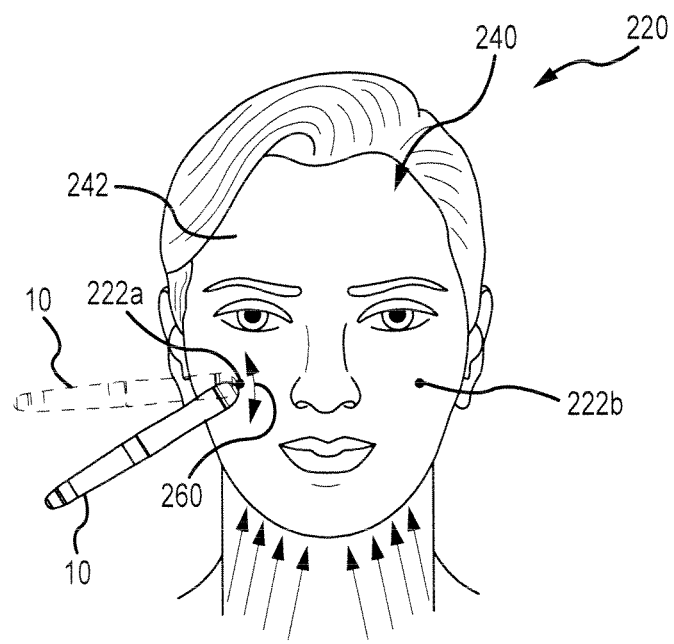
FIG. 22 is a schematic view of an embodiment of a head of the therapeutic wand of FIG. 1 massaging an acupressure point on a human face, in accordance with embodiments of the present disclosure.

FIG. 22 is a schematic view of an embodiment of the head 16 of the therapeutic wand 10 massaging the acupressure point 222a on the human face 220. As described above, practitioners of alternative medicine believe that certain precious stones, semi-precious stones, man-made stones, minerals, or metals have health, beauty and wellness properties. Accordingly, the head 16 may be rubbed against the skin 240, proximate the acupressure points 222 or at other locations, in order to transmit the benefits from the precious stones, semi-precious stones, man-made stones, minerals, or metals in the head 16 to the skin 240. Moreover, the pressure and/or massaging action, illustrated by the arrows 260, may promote circulation and lymph drainage in the skin 240, thereby further improving the physical appearance of the skin 240. As will be appreciated, the head 16 may be rubbed and/or massaged against any portion of the human face 220 and/or skin 240 to receive the benefits promoted by the therapeutic wand 10.

Figure 23:
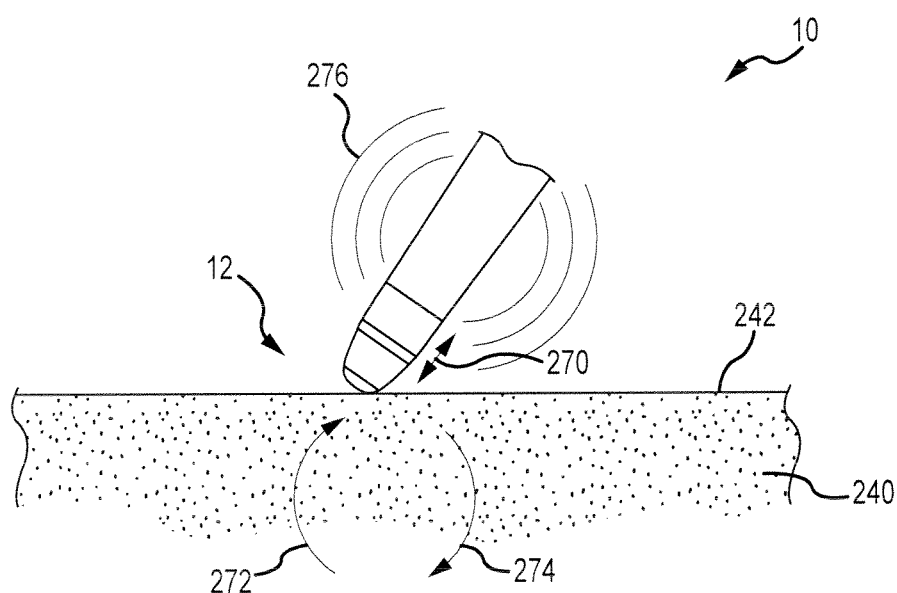
FIG. 23 is a partial schematic view of a tip of the therapeutic wand of FIG. 1 massaging an acupressure point on a human face, in accordance with embodiments of the present disclosure.

FIG. 23 is a partial schematic view of the tip 12 of the therapeutic wand 10 massaging the acupressure point 222 on the human face 220. As described above, the motor 92 positioned within the therapeutic wand 10 transmits vibrational energy to the tip 12. That vibrational energy is further transmitted to the skin 240 via contact between the tip 12 and the surface 242 at the acupressure point 222. As illustrated by the arrows 270, movement of the tip 12 imparts a force to the surface 242 of the skin 240. This force stimulates blood circulation, illustrated by the arrows 272, 274, below the surface 242, thereby promoting health, beauty, and wellness of the skin 240 to promote an improved physical appearance. Moreover, as described above, in certain embodiments the intensity of the vibrational forces generated by the motor 92 may be adjusted. For example, the motor 92 may have different settings that enable different vibrational forces to be transmitted to the skin 240.

Furthermore, as described above, the therapeutic wand 10 includes the magnet 90, which generates a magnetic field represented by the lines 276. This magnetic field emanates out from the therapeutic wand 10 and toward the surface 242 of the skin 240. Practitioners of alternative medicine believe that the magnetic fields improve blood flow in the underlying tissues and/or restore the body's electromagnetic energy balance. As such, the magnetic field 276 produced by the therapeutic wand 10 may serve to facilitate the circulation of blood 272, 274.

Figure 24:
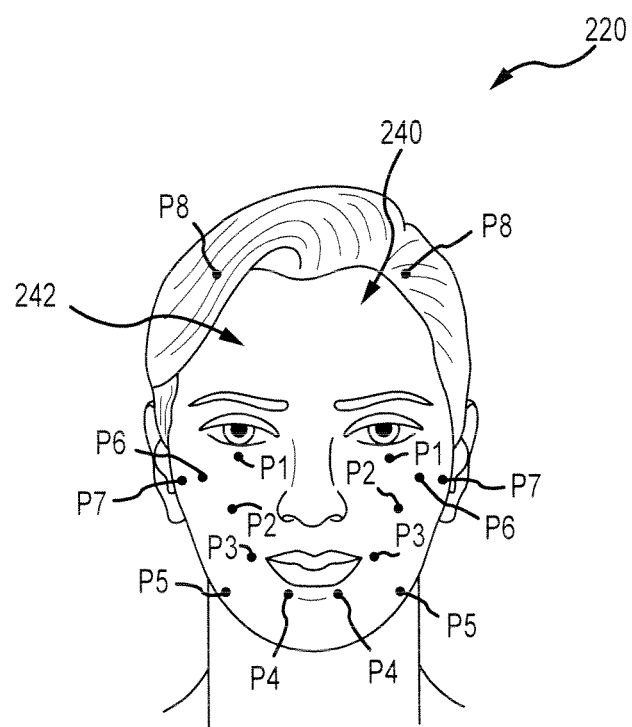
FIG. 24 is a schematic diagram of a human face having multiple acupressure points arranged in a predetermined sequence for activation, in accordance with embodiments of the present disclosure.

FIG. 24 is a schematic diagram of the human face 220 having acupressure points 222 (labeled beginning with the letter in this embodiment) arranged in a predetermined sequence in order to generate one or more health, beauty, and wellness benefits via activation of the acupressure points 222 via the therapeutic wand 10 to generate the improved physical appearance of the skin 240. For example, in certain embodiments, the predetermined sequence may be utilized to reduce wrinkles and/or tighten the appearance of skin to generate the improved physical appearance of the skin 240. In certain embodiments, the series of points may be directed to improving the appearance of the cheeks. In the illustrated embodiment, the user brings the therapeutic wand 10 to the first acupressure points P1, located below the center of the eyes, under the bone surrounding the eye. It should be appreciated that the acupressure point 222 chosen by the user (e.g., the right or the left) may be interchangeable. It should be appreciated that, in operation, the user may perform the predetermined process on one half of the face and then repeat the process on the other half of the face. However, following the order of the points (e.g., following the predetermined pattern) may generate improved physical appearance of the skin 240. After a predetermined period of time has passed (e.g., 5 seconds, 10 seconds, 15 seconds, etc.), the user moves the therapeutic wand 10 to the second acupressure points P2, located directly below the center of the eyes in line with the nostrils. As described above, in certain embodiments, the passage of the predetermined time may be signaled by the indicator 150, for example, via an auditory or visual alarm. Thereafter, the user moves the therapeutic wand 10 to the third acupressure points P3, located below the center of the eyes, in line with the outer corners of the mouth. Then, the user moves the therapeutic wand 10 to the fourth acupressure points P4, located below the mouth, at the center of the chin between the middle and corner of the mouth. Next, the user moves the therapeutic wand to the fifth acupressure points P5, located on the cheek, directly above the angle of the jaw. Thereafter, the user moves the therapeutic wand 10 to the sixth acupressure points P6, directly below the cheek bone, in line with the outer corner of the eyes. Next, the user moves the therapeutic wand 10 the seventh acupressure point P7, located in the depression directly in front of the center of the ear. Then, the user moves the therapeutic wand 10 to the eighth acupressure point P8, located in the hairline, approximately 2 inches from the center. Or located on the forehead, at the bend in the hairline. In certain embodiments, the user may repeat the sequence of points from the beginning a given number of times (e.g., one time, two times, three times, etc.). Moreover, in certain embodiments, the user may repeat activation of each of the acupressure points multiple times before moving on. For example, the user may alternative between the first acupressure points P1 a certain number of times (e.g., one time, two times, three times, any suitable number of times) before moving on to the second acupressure points P2. Moreover, as described above, the user may hold the therapeutic wand 10 to the various acupressure points for the predetermined period of time before moving on to the next point. Furthermore, the user may connect the points in a continuous sweeping motion (e.g., maintaining contact with the skin 240 as the user moves between points) or the user may activate the points without maintaining contact with the skin 240 between the points. In this manner, the user may achieve an improved physical appearance of the skin 240.

Figure 25:
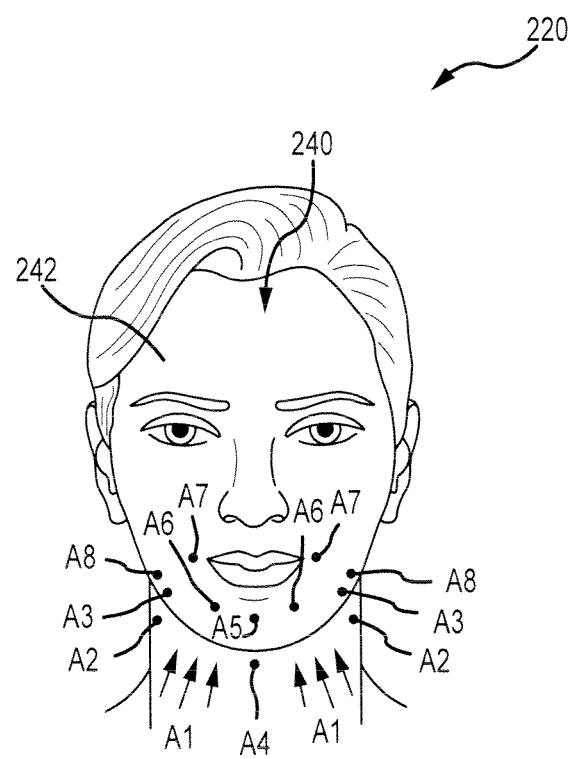
FIG. 25 a schematic diagram of a human face having multiple acupressure points arranged in a predetermined sequence for activation, in accordance with embodiments of the present disclosure.

FIG. 25 is a schematic diagram of the human face 220 having multiple acupressure points 222 arranged in a predetermined sequence in order to generate one or more health, beauty, and wellness benefits via activation of the acupressure points 222 via the therapeutic wand 10. For example, in certain embodiments, the predetermined sequence may be utilized to reduce wrinkles and/or tighten the appearance of skin to generate an improved physical appearance of the skin 240. For example, in certain embodiments, the sequence of points 222 may be directed to improving the appearance of the neck. In the illustrated embodiment, the user begins by moving the therapeutic wand 10 along the neck, as illustrated by the arrows A1. In certain embodiments, the user may sweep the therapeutic wand 10 along the neck a set number of times, such as five times, ten times, twenty times, or any reasonable number of times. Next, after the passage of the predetermined period of time, the user moves the therapeutic wand 10 to the second acupressure point A2, located at the jawline, below the ear. Then, the user moves the therapeutic wand 10 to the third acupressure point A3, located on the neck at the corner of the jawline. Thereafter, the user moves the therapeutic wand 10 to the fourth acupressure point A4, located between the Adam's apple and the chin. Then, the user mover the therapeutic wand 10 to the fifth acupressure point A5, located in the indentation in the center of the chin. Next, the user moves the therapeutic wand 10 to the sixth acupressure point A6, located below the mouth, between the center and the corner of the mouth. Then, the user moves the therapeutic wand 10 to the seventh acupressure point A7, located below the center of the eyes, in line with the outer corners of the mouth. Thereafter, the user moves the therapeutic wand 10 to the eighth acupressure point A8, located on the cheek, directly below the angle of the jaw. In certain embodiments, the user may repeat the sequence of points from the beginning. Moreover, in certain embodiments, the user may repeat activation of each of the acupressure points multiple times before moving on (e.g., one time, two times, three times, etc.). For example, the user may alternative between the first acupressure points P1 a certain number of times (e.g., one time, two times, three times, any suitable number of times) before moving on to the second acupressure points P2. Moreover, as described above, the user may hold the therapeutic wand 10 to the various acupressure points for the predetermined period of time (e.g., 5 seconds, 10 seconds, 15 seconds, etc.) before moving on to the next point. Furthermore, the user may connect the points in a continuous sweeping motion (e.g., maintaining contact with the skin 240 as the user moves between points) or the user may activate the points without maintaining contact with the skin 240 between the points. In this manner, the user may achieve an improved physical appearance of the skin 240.

In certain embodiments, the location of the acupressure points 222 arranged in the predetermined sequence may be particularly selected to treat one or more ailments or conditions or to improve the physical appearance of a certain portion of the human face 220. For example, one sequence of points may be particularly selected to treat wrinkled or sagging skin. However, a different sequence of points may be particularly selected to treat discolored skin or localized pain. As a result, the therapeutic wand 10 may be utilized to target and treat a variety of conditions by following the predetermined sequence of points. Moreover, in certain embodiments, features of the therapeutic wand 10, such as the size, shape, power of the motor 92, the intensity settings of the motor 92, power of the magnet 90, and the like may be modified to treat different conditions. For example, in certain embodiments, the therapeutic wand 10 may be utilized to target back, neck, or shoulder pain. As a result, features of the therapeutic wand 10 may be modified, such as increasing the size of the tip 12, modifying the shape of the tip 12, and/or increasing the power of the motor 92 in order to properly activate the acupressure points 222 identified for those ailments. Moreover, different sequences of points may be generated and utilized by the user based on the therapeutic wand 10 being used. That is, the acupressure points 222 activated, as well as the sequence of activation, may be modified based on the dimensions of the therapeutic wand 10 and/or the ailment and/or goal of treatment.

Figure 26:
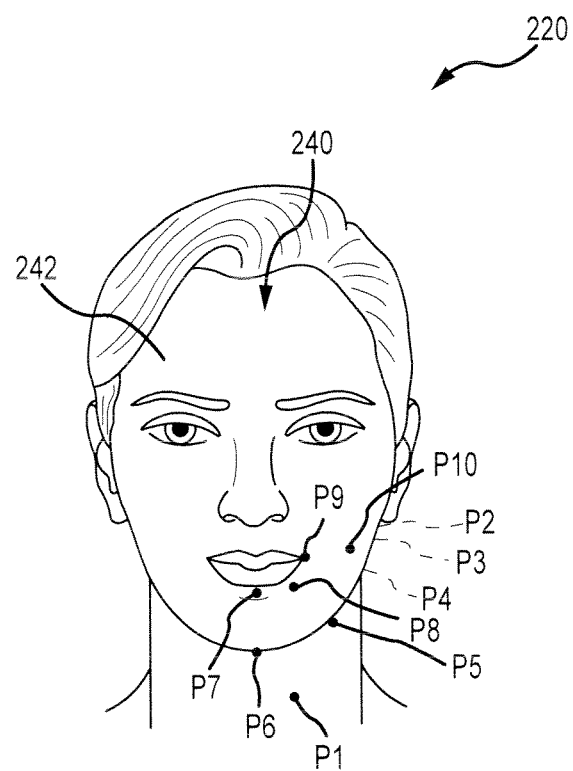
FIG. 26 a schematic diagram of a human face having multiple acupressure points arranged in a predetermined sequence for activation, in accordance with embodiments of the present disclosure.

FIG. 26 is a schematic diagram of the human face 220 having multiple acupressure points 222 (labeled beginning with the letter "P" in this embodiment) arranged in a predetermined sequence in order to generate one or more health, beauty, and wellness benefits via activation of the acupressure points 222 via the therapeutic wand 10 to generate the improved physical appearance of the skin 240. For example, in certain embodiments, the predetermined sequence may be utilized to reduce wrinkles and/or tighten the appearance of skin to generate the improved physical appearance of the skin 240. In certain embodiments, the series of points may be directed to improving the appearance of the neck. In the illustrated embodiment, the user brings the therapeutic wand 10 to the first acupressure point P1, located above the collar bone at the side of the center of the throat. Following the order of the points (e.g., following the predetermined pattern) may generate improved physical appearance of the skin 240. After a predetermined period of time has passed (e.g., 5 seconds, 6 seconds, 7 seconds, 8 seconds, 9 seconds, 10 seconds, 15 seconds, etc.), the user moves the therapeutic wand 10 to the second acupressure point P2, located at the base of the skull. The second acupressure point P2 may be on the back of the neck, approximately three finger-widths from the center of the spine. As described above, in certain embodiments, the passage of the predetermined time may be signaled by the indicator 150, for example, via an auditory or visual alarm. However, in certain embodiments, the user may determine the passage of the predetermined period of time by looking at a clock or counting. Thereafter, the user moves the therapeutic wand 10 to the third acupressure point P3, located on the neck directly below the earlobe. Then, the user moves the therapeutic wand 10 to the fourth acupressure point P4, located on the neck at the corner of the jawline. Next, the user moves the therapeutic wand to the fifth acupressure point P5, located on the neck and under the chin, approximately half way between P4 and the sixth acupressure point P6. Thereafter, the user moves the therapeutic wand 10 to the sixth acupressure point P6, located on the neck under the center of the chin. Next, the user moves the therapeutic wand 10 the seventh acupressure point P7, located in the center of the chin, in the indentation between the chin and lower lip. Then, the user moves the therapeutic wand 10 to the eighth acupressure point P8, located below the mouth, on the chin between the center and corner of the mouth. Next, the user moves the therapeutic wand 10 to the ninth acupressure point P9, located at the corner of the mouth. Thereafter, the user moves the therapeutic wand 10 to the tenth acupressure point P10, located on the cheek, directly above the angle of the jaw. Thereafter, the user may repeat the sequence on the other side of the face and neck. That is, the points P1-10 may be mirrored on the opposite side of the face and neck. In certain embodiments, the user may repeat the sequence of points from the beginning a given number of times (e.g., one time, two times, three times, etc.). Moreover, in certain embodiments, the user may repeat activation of each of the acupressure points multiple times before moving on. For example, the user may alternative between the first acupressure points P1 a certain number of times (e.g., one time, two times, three times, any suitable number of times) before moving on to the second acupressure points P2. Moreover, as described above, the user may hold the therapeutic wand 10 to the various acupressure points for the predetermined period of time before moving on to the next point. Furthermore, the user may connect the points in a continuous sweeping motion (e.g., maintaining contact with the skin 240 as the user moves between points) or the user may activate the points without maintaining contact with the skin 240 between the points. In this manner, the user may achieve an improved physical appearance of the skin 240.

Figure 27:
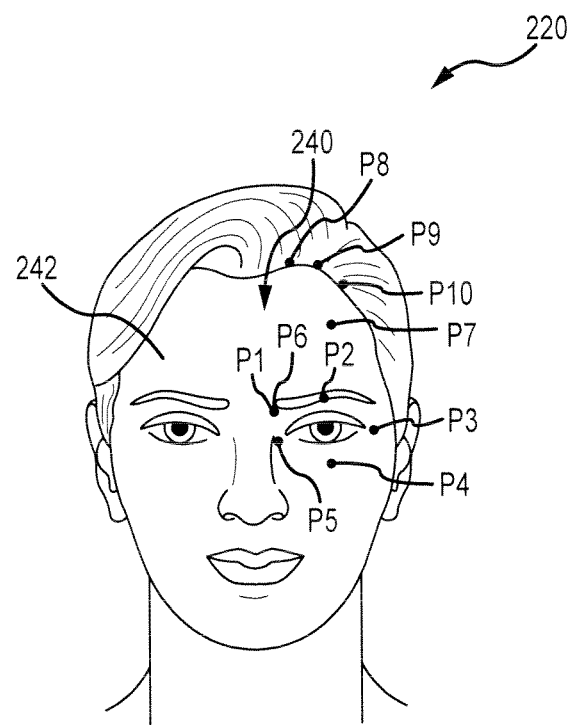
FIG. 27 a schematic diagram of a human face having multiple acupressure points arranged in a predetermined sequence for activation, in accordance with embodiments of the present disclosure.

FIG. 27 is a schematic diagram of the human face 220 having multiple acupressure points 222 (labeled beginning with the letter "P" in this embodiment) arranged in a predetermined sequence in order to generate one or more health, beauty, and wellness benefits via activation of the acupressure points 222 via the therapeutic wand 10 to generate the improved physical appearance of the skin 240. For example, in certain embodiments, the predetermined sequence may be utilized to reduce wrinkles and/or tighten the appearance of skin to generate the improved physical appearance of the skin 240. In certain embodiments, the series of points may be directed to improving the appearance of the eyes. In the illustrated embodiment, the user brings the therapeutic wand 10 to the first acupressure point P1, located at the inner corner of the eyebrow. Following the order of the points (e.g., following the predetermined pattern) may generate improved physical appearance of the skin 240. After a predetermined period of time has passed (e.g., 5 seconds, 6 seconds, 7 seconds, 8 seconds, 9 seconds, 10 seconds, 15 seconds, etc.), the user moves the therapeutic wand 10 to the second acupressure point P2, located at the middle of the eyebrow. As described above, in certain embodiments, the passage of the predetermined time may be signaled by the indicator 150, for example, via an auditory or visual alarm. However, in certain embodiments, the user may look at a clock or count off the predetermined time. Thereafter, the user moves the therapeutic wand 10 to the third acupressure point P3, located at the outer corner of the eye. Then, the user moves the therapeutic wand 10 to the fourth acupressure point P4, located below the center of the eye, directly below the bone surrounding the eye. Next, the user moves the therapeutic wand to the fifth acupressure point P5, located on the side of the nose, at the inner corner of the eye.

Thereafter, the user moves the therapeutic wand 10 to the sixth acupressure point P6, located at the inner corner of the eyebrow. Next, the user moves the therapeutic wand 10 to the seventh acupressure point P7, located on the forehead approximately one inch above the center of the eyebrow. Then, the user moves the therapeutic wand 10 to the eighth acupressure point P8, located in the hairline in line with the inner corner of the eye. Next, the user moves the therapeutic wand 10 to the ninth acupressure point P9, located in the hairline, in line with the center of the eyebrow. Thereafter, the user moves the therapeutic wand 10 to the tenth acupressure point P10, located on the forehead, at the bend in the hairline. Thereafter, the user may repeat the sequence on the other side of the face. That is, the points P1-10 may be mirrored on the opposite side of the face. In certain embodiments, the user may repeat the sequence of points from the beginning a given number of times (e.g., one time, two times, three times, etc.). Moreover, in certain embodiments, the user may repeat activation of each of the acupressure points multiple times before moving on. For example, the user may alternative between the first acupressure points P1 a certain number of times (e.g., one time, two times, three times, any suitable number of times) before moving on to the second acupressure points P2. Moreover, as described above, the user may hold the therapeutic wand 10 to the various acupressure points for the predetermined period of time before moving on to the next point. Furthermore, the user may connect the points in a continuous sweeping motion (e.g., maintaining contact with the skin 240 as the user moves between points) or the user may activate the points without maintaining contact with the skin 240 between the points. In this manner, the user may achieve an improved physical appearance of the skin 240.

Figure 28:
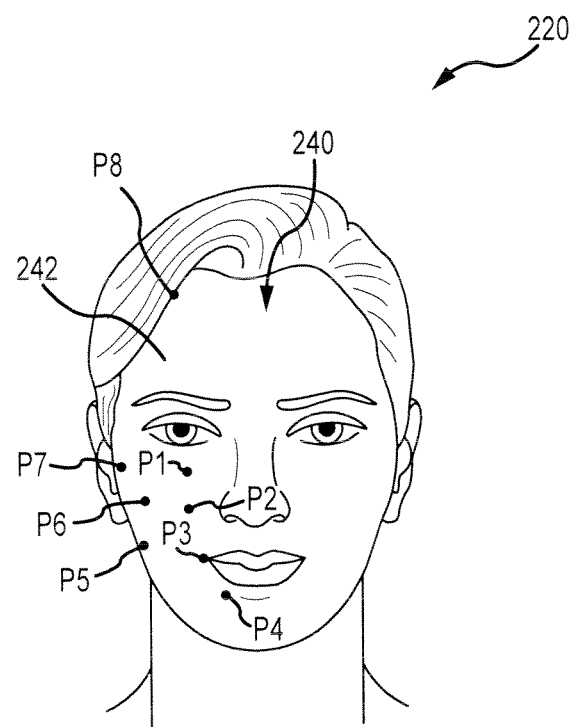
FIG. 28 a schematic diagram of a human face having multiple acupressure points arranged in a predetermined sequence for activation, in accordance with embodiments of the present disclosure.

FIG. 28 is a schematic diagram of the human face 220 having multiple acupressure points 222 (labeled beginning with the letter in this embodiment) arranged in a predetermined sequence in order to generate one or more health, beauty, and wellness benefits via activation of the acupressure points 222 via the therapeutic wand 10 to generate the improved physical appearance of the skin 240. For example, in certain embodiments, the predetermined sequence may be utilized to reduce wrinkles and/or tighten the appearance of skin to generate the improved physical appearance of the skin 240. In certain embodiments, the series of points may be directed to improving the appearance of the cheek. In the illustrated embodiment, the user brings the therapeutic wand 10 to the first acupressure point P1, located below the center of the eye, directly below the bone surrounding the eye. Following the order of the points (e.g., following the predetermined pattern) may generate improved physical appearance of the skin 240. After a predetermined period of time has passed (e.g., 5 seconds, 6 seconds, 7 seconds, 8 seconds, 9 seconds, 10 seconds, 15 seconds, etc.), the user moves the therapeutic wand 10 to the second acupressure point P2, located in line with the center of the eye and the side of the nostril. As described above, in certain embodiments, the passage of the predetermined time may be signaled by the indicator 150, for example, via an auditory or visual alarm. However, in certain embodiments, the user may look at a clock or count off the predetermined time. Thereafter, the user moves the therapeutic wand 10 to the third acupressure point P3, located at the corner of the mouth. Then, the user moves the therapeutic wand 10 to the fourth acupressure point P4, located in the center of the chin between the middle and corner of the mouth. Next, the user moves the therapeutic wand to the fifth acupressure point P5, located on the cheek, directly above the angle of the jaw.

Thereafter, the user moves the therapeutic wand 10 to the sixth acupressure point P6 located directly below the cheekbone, in line with the outer corner of the eye. Next, the user moves the therapeutic wand 10 the seventh acupressure point P7, located in the depression in front of the center of the ear. Then, the user moves the therapeutic wand 10 to the eighth acupressure point P8, located on the forehead, at the bend in the hairline. Thereafter, the user may repeat the sequence on the other side of the face. That is, the points P1-10 may be mirrored on the opposite side of the face. In certain embodiments, the user may repeat the sequence of points from the beginning a given number of times (e.g., one time, two times, three times, etc.). Moreover, in certain embodiments, the user may repeat activation of each of the acupressure points multiple times before moving on. For example, the user may alternative between the first acupressure points P1 a certain number of times (e.g., one time, two times, three times, any suitable number of times) before moving on to the second acupressure points P2. Moreover, as described above, the user may hold the therapeutic wand 10 to the various acupressure points for the predetermined period of time before moving on to the next point. Furthermore, the user may connect the points in a continuous sweeping motion (e.g., maintaining contact with the skin 240 as the user moves between points) or the user may activate the points without maintaining contact with the skin 240 between the points. In this manner, the user may achieve an improved physical appearance of the skin 240.

Figure 29:
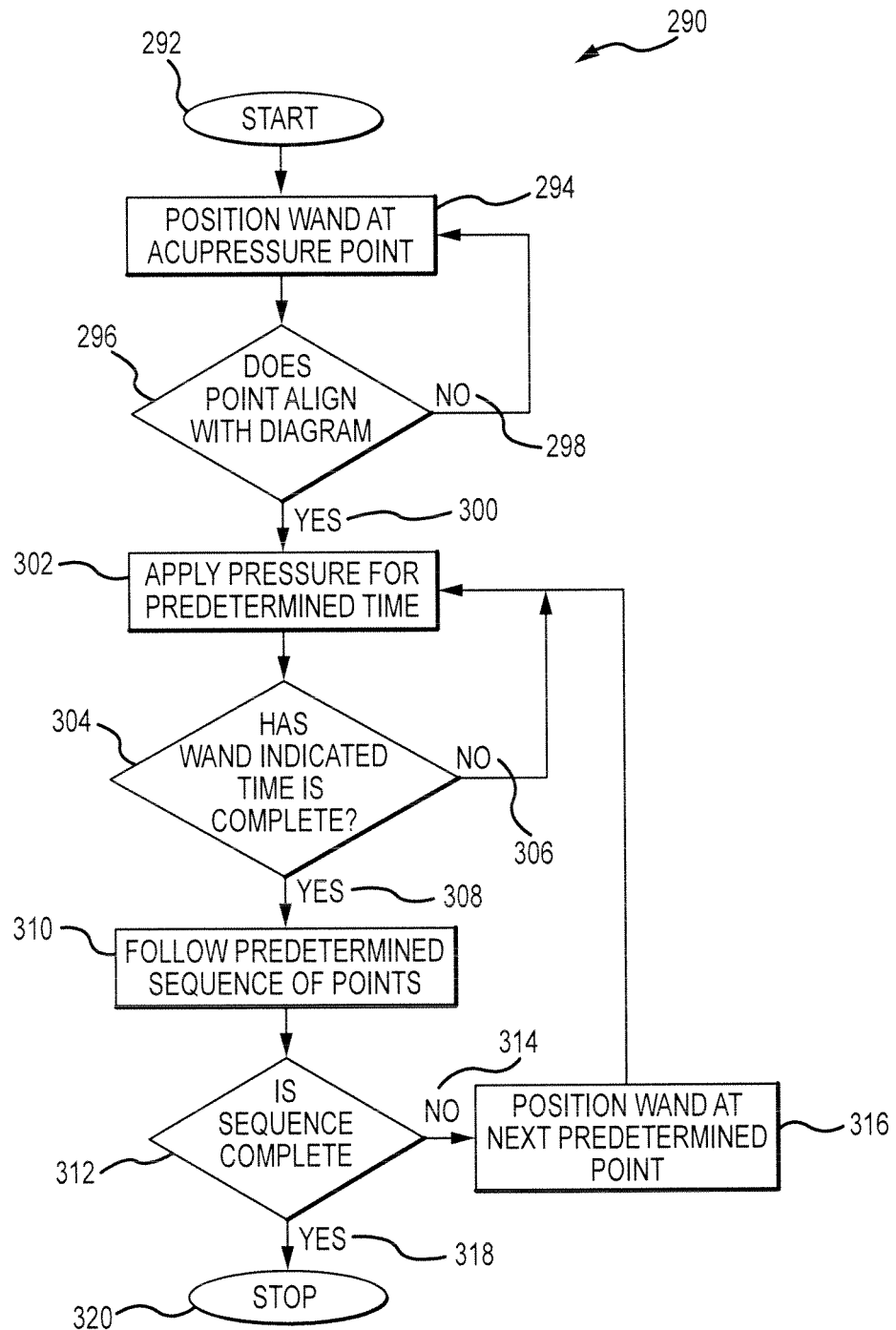
FIG. 29 is a flow chart of a method of using a therapeutic wand, in accordance with embodiments of the present disclosure.

FIG. 29 a flow chart of a method 290 of using the therapeutic wand 10 to improve the physical appearance of the skin 240. In the illustrated embodiment, the method 290 is started (block 292) by a user. The user positions the therapeutic wand 10 at the acupressure point 222 (block 294). For example, the user may position the tip 12 of the therapeutic wand 10 at the acupressure point 222a. Next, the user checks if the therapeutic wand 10 is aligned with the acupressure point 222 by referring to a diagram illustrating the acupressure points 222 on the human face 220 (operator 296). For example, the diagram may be included in the instruction booklet 184, stored on the memory stick 198, or the downloaded instructions the user can load on a personal electronic device. If the therapeutic wand 10 is not aligned with the acupressure point 222 (path 298), then the user returns to block 294 to reposition the therapeutic wand 10. However, if the therapeutic wand 10 is aligned with the acupressure point 222 (path 300), the user continues the method 290 and applies pressure to the acupressure point 222 for a predetermined period of time (block 302). For example, in certain embodiments, the predetermined period of time may be 5 seconds, 10 seconds, 15 seconds, 20 seconds, or any reasonable period of time to generate an improved physical appearance of the skin 240. As described above, the printed circuit board 128 may be communicatively connected to the timer 164 to track the duration of time the tip 12 is positioned against the skin 240. Moreover, the indicator 150 may be utilized to inform the user when the predetermined period of time has passed. For example, the indicator 150 may include an auditory alarm that informs the user when the period of time has passed. In this manner, the user can receive feedback from the therapeutic wand 10, thereby improving operation and the likelihood of receiving the desired results from the therapeutic wand 10. Furthermore, the pressure applied may be associated with the intensity of the motor 92. For example, in certain embodiments, the motor 92 may operate at different intensities (e.g., light, medium, or heavy) to generate different levels of vibrational force. Moreover, different levels of force may be utilized at different points on the human face 220. For example, a light intensity may be used on the eyes 228, while a heavier intensity may be used on the cheeks 226.

Continuing with the method 290, the user determines if the therapeutic wand 10 has been held against the skin 240 for the predetermined time (operator 304). For example, as described above, this determination may be provided by the indicator 150 of the therapeutic wand 10. If the predetermined time has not passed (path 306), the user continues to apply pressure to the acupressure point 222. However, if the predetermined time has passed (path 308) then the user moves the therapeutic wand 10 to a different acupressure point 222 to follow a predetermined path of acupressure points 222 (block 310). For example, as described above, the instruction booklet 184 may include a series of acupressure points 222 that the user may activate with the therapeutic wand 10 to improve the physical appearance of the skin 240. Accordingly, the user will follow these instructions and move along the path between points 222. Next, the user determines if the sequence is complete (operator 312). For example, the user may look at the instruction booklet 184 to determine whether they have followed the complete predetermined path. If the user has not completed the sequence of points 222 (path 314), the user positions the therapeutic wand 10 at the next acupressure point 222 (block 316). From there, the user returns to block 302 to apply pressure to the acupressure point 222. However, if the predetermined sequence is complete (path 318) the user stops (block 320). In this manner, the user can effectively operate the therapeutic wand 10 along the predetermined path in order to generate an improved physical appearance of the skin 240.

Figure 30:
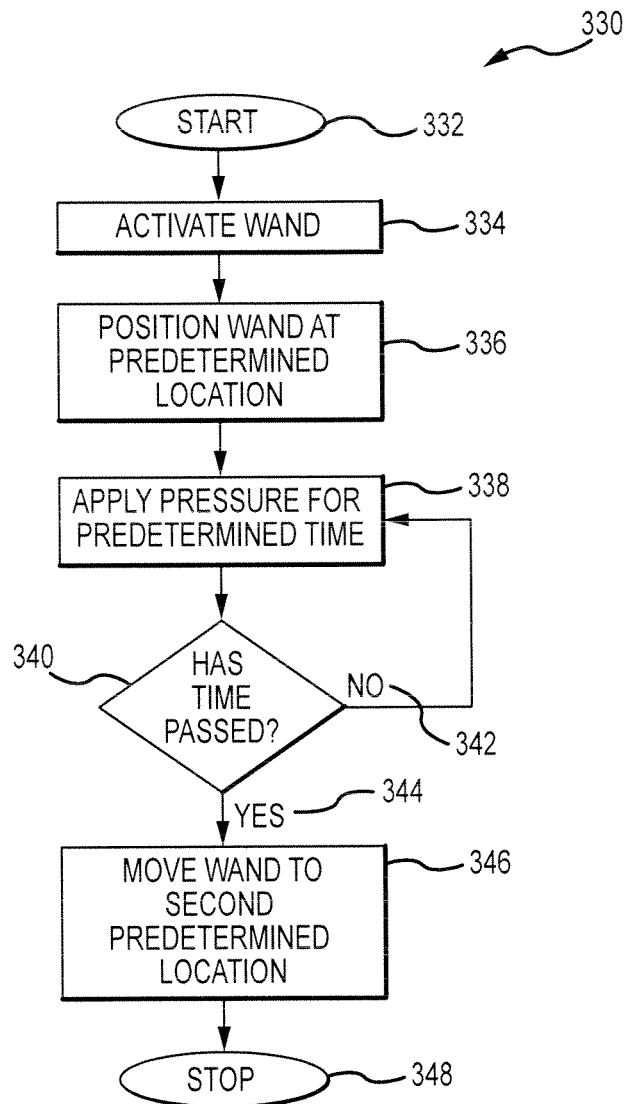
FIG. 30 is a flow chart of a method of using a therapeutic wand, in accordance with embodiments of the present disclosure.

FIG. 30 is a flow chart of a method 330 of using the therapeutic wand 10 to improve the physical appearance of the skin 240. In the illustrated embodiment, the method 330 is started (block 332) by a user. For example, the user may be holding the therapeutic wand 10 by the grip 22. Next, the therapeutic wand 10 is activated (block 334). For example, the user may activate the switch 28 by twisting the therapeutic wand 10 or the tact switch 122 by pressing against it. Activation of the therapeutic wand 10 electrically couples the battery 104 to the motor 92 thereby generating vibrational energy that can be applied to the skin 240 via the tip 12. Moreover, in embodiments where the motor 92 has multiple settings, activation may include adjusting the motor 92 to be at the proper setting depending on the treatment and/or location of the therapeutic wand 10 relative to the human face 220. For example, lighter intensities may be used around the eyes 228. Thereafter, the therapeutic wand 10 is positioned at a predetermined location, such as the acupressure point 222 (block 336). As described above, the predetermined location may be determined by the path or instructions located in the instruction booklet 184. Next, the user will position the tip 12 of the therapeutic wand 10 against the skin surface 242 and apply pressure for a predetermined time (block 338). As described above, the predetermined time may be measured by the timer 164, sensor 166, and/or printed circuit board 128 of the therapeutic wand 10. Thereafter, the user determines whether the predetermined time has passed (operator 340). For example, the user may be notified by the indicator 150 when the predetermined time has passed. If the time has not passed (path 342), the user continues to apply pressure for the predetermined time (block 338). However, if the predetermined time has passed (path 344), then the user may continue with the method 330 by moving the therapeutic wand 10 to a second predetermined location (block 346). For example, the second predetermined location may be a different acupressure point 222. Thereafter, the user can stop the method (block 348). In this manner, the therapeutic wand 10 may be utilized to apply pressure to one or more acupressure points 222 for a predetermined period of time to generate an improved physical appearance of the skin 240.

As will be understood by those skilled in the art, additional protocols may be used with the wand 10 for application and benefits related to massage and/or acupuncture or other therapeutic uses. For example, protocols may also be established for neck pain, shoulder pain, eye strain, sinus issues, headaches, allergies, and other head and face related pains, illness, or therapeutic needs/desires. It will also be understood by those skilled in the art that other shapes of wands for these types of therapeutic uses may be used as well.

Figure 31:
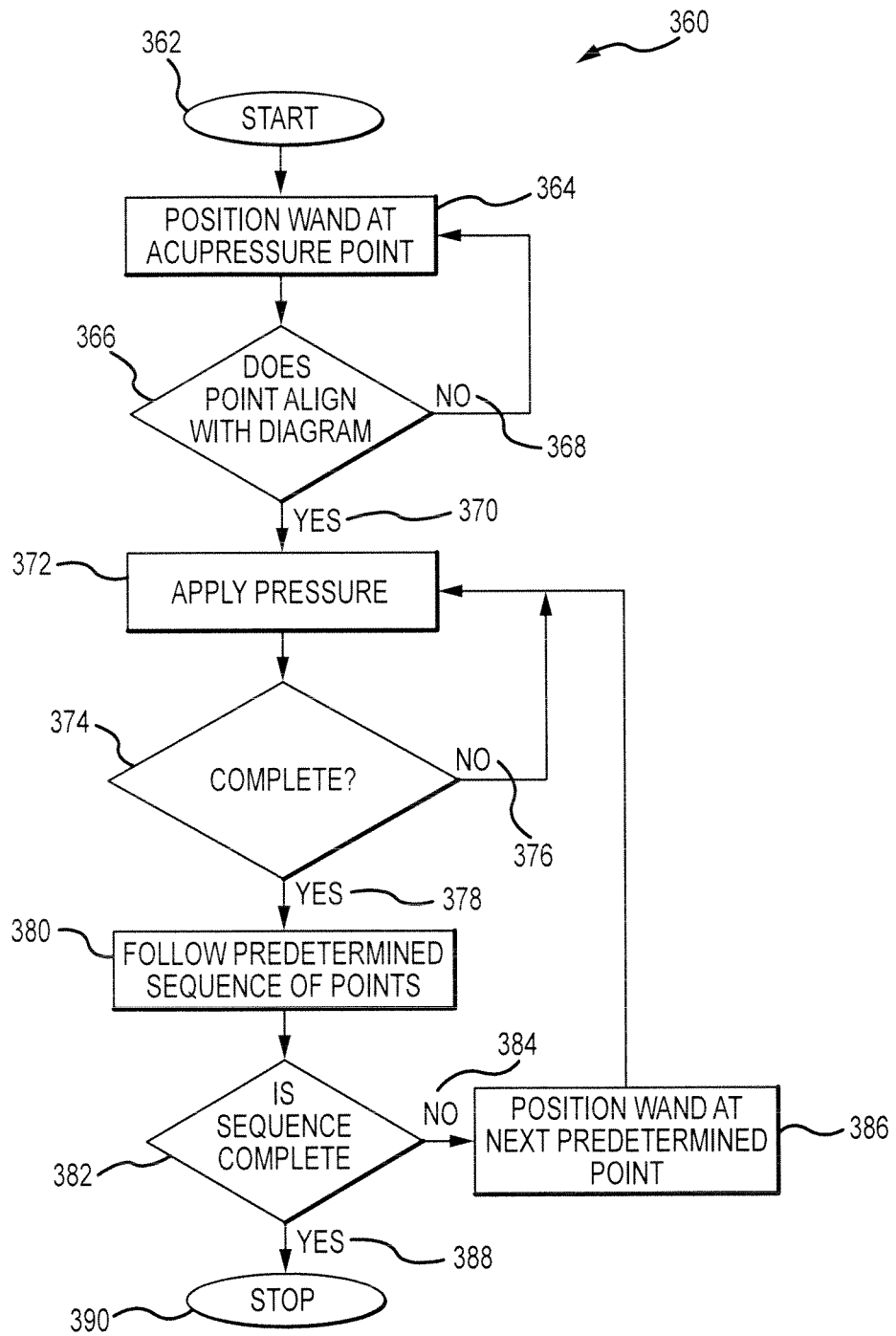
FIG. 31 is a flow chart of a method of using a therapeutic wand, in accordance with embodiments of the present disclosure.

FIG. 31 a flow chart of a method 360 of using the therapeutic wand 10 to improve the physical appearance of the skin 240. In the illustrated embodiment, the method 360 is started (block 362) by a user. The user positions the therapeutic wand 10 at the acupressure point 222 (block 364). For example, the user may position the tip 12 of the therapeutic wand 10 at the acupressure point 222*a*. Next, the user checks if the therapeutic wand 10 is aligned with the acupressure point 222 by referring to a diagram illustrating the acupressure points 222 on the human face 220 (operator 366). For example, the diagram may be included in the instruction booklet 184, stored on the memory stick 198, or the downloaded instructions the user can load on a personal electronic device. If the therapeutic wand 10 is not aligned with the acupressure point 222 (path 368), then the user returns to block 364 to reposition the therapeutic wand 10. However, if the therapeutic wand 10 is aligned with the acupressure point 222 (path 370), the user continues the method 290 and applies pressure to the acupressure point 222 for a predetermined period of time (block 372). For example, in certain embodiments, the predetermined period of time may be 5 seconds, 10 seconds, 15 seconds, 20 seconds, or any reasonable period of time to generate an improved physical appearance of the skin 240. In certain embodiments, the predetermined period of time may be relayed to the user via the instruction booklet 184, the memory stick 198, or other downloadable instructions. The user may look at a clock to track the period of time or mentally keep track of the predetermined period of time. Furthermore, the pressure applied may be associated with the intensity of the motor 92. For example, in certain embodiments, the motor 92 may operate at different intensities (e.g., light, medium, or heavy) to generate different levels of vibrational force. Moreover, different levels of force may be utilized at different points on the human face 220. For example, a light intensity may be used on the eyes 228, while a heavier intensity may be used on the cheeks 226.

Continuing with the method 360, the user determines if the therapeutic wand 10 has been held against the skin 240 for the predetermined time (operator 374). If the predetermined time has not passed (path 376), the user continues to apply pressure to the acupressure point 222. However, if the predetermined time has passed (path 378) then the user moves the therapeutic wand 10 to a different acupressure point 222 to follow a predetermined path of acupressure points 222 (block 380). For example, as described above, the instruction booklet 184 may include a series of acupressure points 222 that the user may activate with the therapeutic wand 10 to improve the physical appearance of the skin 240. Accordingly, the user will follow these instructions and move along the path between points 222. Next, the user determines if the sequence is complete (operator 382). For example, the user may look at the instruction booklet 184 to determine whether they have followed the complete predetermined path. If the user has not completed the sequence of points 222 (path 384), the user positions the therapeutic wand 10 at the next acupressure point 222 (block 386). From there, the user returns to block 302 to apply pressure to the acupressure point 222. However, if the predetermined sequence is complete (path 388) the user stops (block 390). In this manner, the user can effectively operate the therapeutic wand 10 along the predetermined path in order to generate an improved physical appearance of the skin 240.

Figure 32:
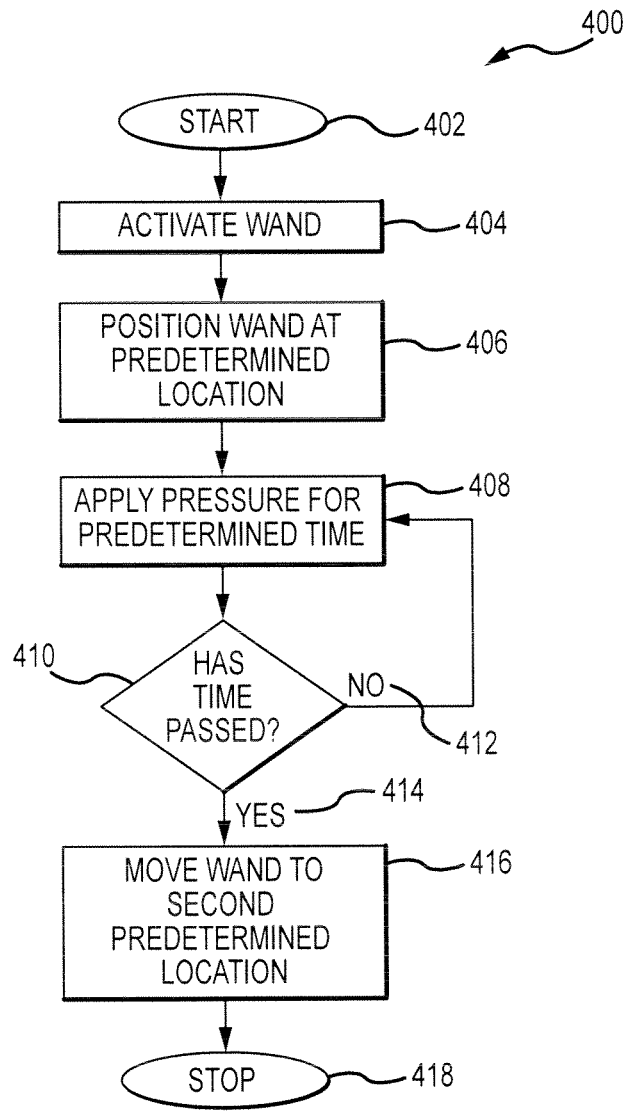
FIG. 32 is a flow chart of a method of using a therapeutic wand, in accordance with embodiments of the present disclosure.

FIG. 32 is a flow chart of a method 400 of using the therapeutic wand 10 to improve the physical appearance of the skin 240. In the illustrated embodiment, the method 400 is started (block 402) by a user. For example, the user may be holding the therapeutic wand 10 by the grip 22. Next, the therapeutic wand 10 is activated (block 404). For example, the user may activate the switch 28 by twisting the therapeutic wand 10 or the tact switch 122 by pressing against it. Activation of the therapeutic wand 10 electrically couples the battery 104 to the motor 92, thereby generating vibrational energy that can be applied to the skin 240 via the tip 12. Moreover, in embodiments where the motor 92 has multiple settings, activation may include adjusting the motor 92 to be at the proper setting depending on the treatment and/or location of the therapeutic wand 10 relative to the human face 220. For example, lighter intensities may be used around the eyes 228. Thereafter, the therapeutic wand 10 is positioned at a predetermined location, such as the acupressure point 222 (block 406). As described above, the predetermined location may be determined by the path or instructions located in the instruction booklet 184. Next, the user will position the tip 12 of the therapeutic wand 10 against the skin surface 242 and apply pressure for a predetermined time (block 408). As described above, the predetermined time may be provided to the user in the instruction booklet 184 or downloadable instructions. Thereafter, the user determines whether the predetermined time has passed (operator 410). For example, the user may look at a clock or count the time off. If the time has not passed (path 412), the user continues to apply pressure for the predetermined time (block 4088). However, if the predetermined time has passed (path 414), then the user may continue with the method 400 by moving the therapeutic wand 10 to a second predetermined location (block 416). For example, the second predetermined location may be a different acupressure point 222. Thereafter, the user can stop the method (block 418). In this manner, the therapeutic wand 10 may be utilized to apply pressure to one or more acupressure points 222 for a predetermined period of time to generate an improved physical appearance of the skin 240.

As will be understood by those skilled in the art, additional protocols may be used with the wand 10 for application and benefits related to massage and/or acupuncture or other therapeutic uses. For example, protocols may also be established for neck pain, shoulder pain, eye strain, sinus issues, headaches, allergies, and other head and face related pains, illness, or therapeutic needs/desires. It will also be understood by those skilled in the art that other shapes of wands for these types of therapeutic uses may be used as well.

As described in detail above, embodiments of the present disclosure include the therapeutic wand 10, the therapeutic wand kit 180, and methods of operation 290, 330. For example, the therapeutic wand 10 includes the tip 12 at the first end 14 and the head 16 at the second end 18. The tip 12 is utilized to stimulate one or more acupressure points 222, such as those located on the human face 220. The therapeutic wand 10 includes the motor 92 for generating vibrational energy to stimulate and massage the skin surface 242 to promote blood circulation and lymph drainage, thereby promoting an improved physical appearance of the skin 240. Moreover, in certain embodiments, the therapeutic wand 10 includes the printed circuit board 128 and the indicator 150 for notifying the user when a period of time has passed. For example, in certain embodiments, the user may apply pressure against the skin surface 242 via the tip 12 for a predetermined period of time. The printed circuit board 128 may be configured to determine the time passed and send a signal to the indicator 150 to notify the user, such as via an auditory alarm or a visual alarm. Moreover, embodiments of the present disclosure include the kit 180 comprising the therapeutic wand 10, the container 182, and the instruction booklet 184. For example, the kit 180 may be sold to users as a complete at-home beauty, health, and wellness regimen so that users can improve the physical appearance of their skin 240 through use of the therapeutic wand kit 180. Moreover, in certain embodiments, the kit 180 may include additional features, such as the covering 186 and replacement parts. Furthermore, embodiments of the present disclosure include methods of operation for the therapeutic wand 10. For example, the methods 290, 330 may include positioning the therapeutic wand 10 at acupressure points 222, applying pressure to the skin surface 242, determining whether the predetermined period of time has passed, and moving the therapeutic wand 10 after the predetermined period of time has passed. In this manner, the user can utilize the therapeutic wand 10 to improve the physical appearance of the skin 240.

This application claims priority to and the benefit of U.S. Provisional Patent Application No. 62/360,538 filed on Jul. 11, 2016 titled "Therapeutic Wand System, Kit, and Method" and which is incorporated herein by reference in its entirety.

The foregoing disclosure and description of the disclosed embodiments is illustrative and explanatory of the embodiments of the invention. Various changes in the details of the illustrated embodiments can be made within the scope of the appended claims without departing from the true spirit of the disclosure. The embodiments of the present disclosure should only be limited by the following claims and their legal equivalents.

That claimed is:

1. A method for operating an at-home therapeutic wand, the method comprising:
   positioning a tip of a therapeutic wand proximate a first predetermined location, the first predetermined location being proximate a first one or more selected locational points, the tip of the therapeutic wand positioned to have a substantially smooth surface, the therapeutic wand further having a housing, a motor positioned in the housing, a magnet positioned within the housing, a timer circuit positioned in the housing and positioned to include a timer and a processor positioned to be responsive to the timer, and an indicator connected to the timer circuit, the processor positioned to determine a lapse of a first predetermined time period and a second predetermined time period, the indicator positioned responsive to the timer circuit to provide indication after the lapse of the first and second predetermined time periods, and the processor positioned to continue to determine the lapse of subsequent predetermined time periods;

applying pressure to the first predetermined location via the therapeutic wand, the therapeutic wand positioned to have the tip to bear against a surface when proximate the first predetermined location;

activating the motor positioned within the housing of the therapeutic wand, the motor providing vibrational energy that is transferred from the tip of the therapeutic wand to the surface at the first predetermined location;

activating the magnet positioned within a housing of the therapeutic wand during the time period of activation of the motor at the first predetermined location, the magnet generating a magnetic field that is transferred from the tip of the therapeutic wand to the surface;

holding the therapeutic wand against the first predetermined location for the first predetermined time period, the first predetermined time period being signaled by the indicator positioned in the therapeutic wand;

moving the therapeutic wand to a second predetermined location, the second predetermined location being proximate a second one or more selected locational points and being spaced apart from the first predetermined location;

activating the motor positioned within a housing of the therapeutic wand thereby to provide vibrational energy that is transferred from the tip of the therapeutic wand to the surface at the second predetermined location;

activating the magnet positioned within a housing of the therapeutic wand during the time period of activation of the motor at the second predetermined location, the magnet generating a magnetic field that is transferred from the tip of the therapeutic wand to the surface;

holding the therapeutic wand against the second predetermined location for the second predetermined time period, the second predetermined time period being signaled by the indicator positioned in the therapeutic wand; and continuing to follow a sequence of subsequent predetermined locations, each of the subsequent predetermined locations of the sequence of predetermined locations corresponding to one or more acupressure points, the first and second predetermined locations and the sequence of subsequent predetermined locations forming a preselected pattern when utilizing the therapeutic wand.

2. The method of claim 1, further comprising massaging one or more locational points with a head formed on an opposite end of the therapeutic wand than the tip, the head comprising a precious stone, a semi-precious stone, a man-made stone, a mineral, or a metal.

3. The method of claim 1, wherein the tip includes a cavity to receive a conductive material connected to the magnet so as to enhance the conductive properties of the magnet arranged to be positioned within the housing.

4. The method of claim 1, wherein the housing of the therapeutic wand has a cylindrical shape.

5. The method of claim 1, wherein moving the therapeutic wand to the second predetermined location includes:
lifting the therapeutic wand off from the first predetermined location to the second predetermined location.

6. The method of claim 1, wherein the lapse of the first predetermined time period and the second predetermined time period is different from the lapse of at least one of the subsequent predetermined time periods.

7. The method of claim 1, wherein the magnet includes a solid electromagnet having a cylindrical shape positioned to substantially fill interstitial void space within a portion of the housing of the therapeutic wand, the magnet generating a magnetic field via an electrical coupling to the motor.

8. The method of claim 1, wherein the motor includes an off-center weight rotating about a shaft to generate the vibrational energy.

9. The method of claim 1, wherein the timer resets after a predetermined period of time.

10. A method for operating an at-home therapeutic wand, the method comprising:

positioning a tip of a therapeutic wand proximate a first predetermined location, the first predetermined location associated with a first one or more selected locational points, the tip of the therapeutic wand positioned to have a substantially smooth surface, the therapeutic wand further having a housing, a motor positioned in the housing, a magnet positioned within the housing, a timer circuit positioned in the housing and positioned to include a timer and a processor positioned to be responsive to the timer, and an indicator connected to the timer circuit, the processor positioned to determine a lapse of a first predetermined time period and a second predetermined time period, the indicator positioned responsive to the timer circuit to provide indication after the lapse of the first and second predetermined time periods, and the processor positioned to continue to determine the lapse of subsequent predetermined time periods;

applying pressure to the first predetermined location via the therapeutic wand, the therapeutic wand positioned to have the tip to bear against a surface when proximate the first predetermined location;

activating the motor positioned within the housing of the therapeutic wand, the motor providing vibrational energy that is transferred from the tip of the therapeutic wand to the surface at the first predetermined location;

activating the magnet positioned within a housing of the therapeutic wand during the time period of activation of the motor at the first predetermined location, the magnet generating a magnetic field that is transferred from the tip of the therapeutic wand to the surface;

holding the therapeutic wand against the first predetermined location for the first predetermined time period;

moving the therapeutic wand to a second predetermined location, the second predetermined location being a second one or more selected locational points and being spaced apart from the first predetermined location;

activating the motor positioned within a housing of the therapeutic wand thereby to provide vibrational energy that is transferred from the tip of the therapeutic wand to the surface at the second predetermined location;

activating the magnet positioned within a housing of the therapeutic wand during the time period of activation of the motor at the second predetermined location, the magnet generating a magnetic field that is transferred from the tip of the therapeutic wand to the surface;

holding the therapeutic wand against the second predetermined location for a second predetermined time period; and performing a sequence of subsequent predetermined locations, each of the subsequent predetermined locations of the sequence of predetermined locations associated with one or more acupressure points, the first and second predetermined locations and the subsequent sequence of predetermined locations forming a preselected pattern to define a therapeutic regimen when utilizing the therapeutic wand.

11. The method of claim 10, further comprising massaging one or more locational points with a head formed on an opposite end of the therapeutic wand than the tip, the head comprising one or more of a precious stone, a semi-precious stone, a man-made stone, a mineral, and a metal.

\* \* \* \* \*